(12) United States Patent
Shachaf

(10) Patent No.: US 11,872,111 B2
(45) Date of Patent: Jan. 16, 2024

(54) PATCHES FOR LOCALIZED USE

(71) Applicant: ORLUCENT INC., Los Gatos, CA (US)

(72) Inventor: Catherine Shachaf, Los Gatos, CA (US)

(73) Assignee: ORLUCENT INC.

(*) Notice: Subject to any disclaimer, the term of this patent is extended or adjusted under 35 U.S.C. 154(b) by 0 days.

(21) Appl. No.: 17/209,369

(22) Filed: Mar. 23, 2021

(65) Prior Publication Data

US 2022/0304864 A1 Sep. 29, 2022

(51) Int. Cl.
*A61F 13/02* (2006.01)
*A61L 15/22* (2006.01)
*A61F 13/00* (2006.01)

(52) U.S. Cl.
CPC .......... *A61F 13/0259* (2013.01); *A61L 15/22* (2013.01); *A61F 2013/00097* (2013.01); *A61F 2013/00285* (2013.01); *A61L 2300/442* (2013.01); *A61L 2300/45* (2013.01); *A61L 2400/12* (2013.01)

(58) Field of Classification Search
CPC .............. A61K 9/7084; A61K 49/0052; A61K 49/0021; A61K 49/0032; B32B 2307/724; B32B 2309/105; B32B 2556/00; B32B 37/025; B32B 38/0004; A61F 13/0246; A61F 13/0283; A61F 15/005; A61F 13/0259; A61F 2013/00097; A61F 2013/00285; A61F 13/0233; A61F 13/00063; B01L 2200/0652; B01L 3/502761; B01L 3/502784; G01N 29/222; A61L 15/22; A61L 2300/442; A61L 2300/45; A61L 15/58; A61L 2400/12; A61L 15/54

See application file for complete search history.

(56) References Cited

U.S. PATENT DOCUMENTS

| | | | |
|---|---|---|---|
| 5,109,874 A | 5/1992 | Bellingham et al. | |
| 7,395,111 B2 | 7/2008 | Levin et al. | |
| 7,582,069 B2 | 9/2009 | Laurent et al. | |
| 10,245,272 B2 | 4/2019 | Kravchenko et al. | |
| 10,739,908 B2 | 8/2020 | Franklin et al. | |
| 10,835,672 B2 | 11/2020 | Dobbles et al. | |
| 2003/0124293 A1 | 7/2003 | Sher et al. | |
| 2003/0225360 A1* | 12/2003 | Eppstein | A61N 1/327 604/19 |
| 2009/0043236 A1 | 2/2009 | Kawamura et al. | |
| 2010/0221313 A1* | 9/2010 | Smith | A61K 9/7084 424/448 |
| 2014/0120564 A1* | 5/2014 | Workman | A61B 5/418 435/14 |
| 2016/0199230 A1* | 7/2016 | Doshi | A61F 13/58 156/219 |
| 2018/0161252 A1 | 6/2018 | Francis et al. | |
| 2020/0405331 A1 | 12/2020 | Kendall | |

* cited by examiner

*Primary Examiner* — Anna R Falkowitz
(74) *Attorney, Agent, or Firm* — Dave Law Group LLC; Raj S. Dave

(57) ABSTRACT

The present invention relates to a device and a method. The device of the present invention comprising a patch comprising: a substrate, and an adhesive on the substrate. Further, the patch is configured to be attached to a skin via the adhesive to form a pocket between the patch and the skin, to allow introduction of a material into the pocket, and to hold the material within the pocket.

16 Claims, 6 Drawing Sheets

PATCHES FOR LOCALIZED USE

FIELD OF THE INVENTION

This invention relates to a device comprising a patch, a method for making the device and a method for applying the device on a skin and providing material to the skin through the patch without breaching the skin surface.

BACKGROUND

A Bandage or patch in medical terms relates to a strip of woven material used to bind up a wound or to protect an injured part of the body. Bandages for wounds or burns are commonly composed of sterile absorbent dressings that are fastened in place by separate fasteners such as tape, adhesives, compressive textiles, or ties [1]. These patches generally allow the application of a substance, chemical, compound, imaging agent or drug on the skin. Other prior art bandages may be made of materials that are gas impermeable or liquid impermeable, however, such bandages are constructed to only partially shield a wound to allow air to enter the wound area to provide circulation. Thus, while the bandage material is gas impermeable or liquid impermeable, the bandage, when placed on the wound permits the wound to breath [2].

WO2016176514 discloses "a bandage comprising a sterile dressing a conditioned medium applied to the sterile dressing, wherein the conditioned medium is contained in nanocapsules, wherein the nanocapsules are applied to the sterile dressing as an aqueous suspension and air dried. The method further comprising adding a liquid to the bandage."

U.S. Ser. No. 00/510,9874A discloses "A dynamic wound patch having a gas and liquid impermeable member that is adhesively sealed to the skin around a wound to temporarily form a barrier over the wound to prevent the ingress or egress of gases and liquids through the wound patch to permit a user to engage in physical activity without concern for contaminants entering or leaving the wound area and a method of creating an in-situ, non-stick island on a wound patch.

U.S. Pat. No. 4,776,331A discloses "A bandage useful, for instance, in medical applications includes a rupturable sheet or strip having encapsulated fluid (liquid or gas). The sheet or strip is disposed between the body portion to be bandaged and the outer surface of the bandage. The sheet or strip ruptures when a predetermined pressure is exceeded, thereby releasing the fluid for indicating that the bandage is applied too tightly. When the fluid is a liquid, such as a dye, the released liquid will stain the bandage. When the substance is a gaseous substance, the release of the gas will be sensed. When a plurality of strips are used, one strip may contain a liquid and another one a gaseous substance where the strips may rupture at different predetermined pressures."

Further, ring stickers or patches can be used for imaging. An embodiment relates to WO200640773 discloses "Dermal Tissue Inspection (DTI) apparatus including a contact face for intimate placement on a skin site, a multi-spectral irradiation arrangement for irradiating dermal tissue through an aperture in the contact face at least two different wavelengths, a digital imaging arrangement for capturing digital images of irradiated dermal tissue through the aperture for imaging the dermal tissue at different imaging depths relative to the skin site's surface corresponding to the at least two different wavelengths, and a computing unit for processing the digital images for displaying clinical information on a display screen including clinical images at different imaging depths relative to the skin site's surface. The DTI apparatus is preferably used in conjunction with self-adhesive ring stickers for encircling skin patches at a skin site that have machine readable identification information for identification purposes."

Despite all this, patches which can allow the introduction of a material after the application of the patch are not disclosed. None of the patches that allow the application of imaging agents after the application of the patch are disclosed.

The present invention allows introduction of a material such as a liquid in a localized manner after the application of the patch on the skin. In one embodiment, the materials that are activated are used for imaging.

SUMMARY

The present invention relates to a device comprising a patch with substrate and adhesive.

An embodiment relates to the patch attached to a skin via the adhesive to form a pocket between the patch and the skin. This allows the introduction of a material into the pocket, and to hold the material within the pocket.

In an embodiment, the device further comprises a peelable liner and/or an opening.

In another embodiment, the peelable liner is below the patch and attached to the patch via the adhesive to form the pocket between the patch and the peelable liner.

In an embodiment, the opening in the device further comprising a flap.

In an embodiment, the flap is same as the substrate.

In an embodiment, the flap is different than the substrate.

In an embodiment, the flap comprises a net structure to hold a surface tension of a liquid.

In an embodiment, the substrate comprises a non-permeable material and/or a permeable membrane.

In an embodiment, the substrate and the adhesive are biocompatible and/or compatible with a penetration enhancer.

In an embodiment, the penetration enhancer comprises sulphoxide, azone, pyrrolidone, alcohol and alkanol, glycol, surfactant and/or terpenes or combination thereof.

In an embodiment, the substrate and the adhesive are compatible with DMSO.

In an embodiment, the substrate is flexible.

In an embodiment, the material in the pocket comprises a conditioning liquid, a molecular dye, a tag, a nanoparticle, a radionucleotide and/or a combination thereof.

In an embodiment, the material in the pocket is configured to be activated in a condition and to react with the skin.

In an embodiment, the condition comprises a radiation, a heat, a mixing with a second material and/or a combination thereof.

In an embodiment, the patch is placed on a non-breached skin surface and/or a breached skin surface.

In an embodiment, the device is configured for an imaging purpose or a localized drug usage or a combination thereof.

In an embodiment, the device further comprises a peelable liner, wherein the peelable liner is below the patch and attached to the patch via the adhesive to form the pocket between the patch and the peelable liner.

In an embodiment, the pocket comprises a space or a pattern.

In an embodiment, the opening comprises a protrusion or a tubular structure.

In an embodiment, the said protrusion or said tubular structure comprises a clamp configured to open or close the opening.

In an embodiment, the present invention relates to a method comprising:

a. fixing a patch of a device to a skin forming a pocket between the skin and the patch;
b. introducing a material into the pocket; and
c. allowing the material to react with the skin,
wherein the patch comprising a substrate, an adhesive and an opening in the substrate;
wherein the material in the pocket gets activated.

In an embodiment, the material is activated in a condition, comprising a radiation, a heat, a mixing with a second material and/or a combination thereof.

In an embodiment, the material in the pocket is configured to allow a skin-substance to emerge from the skin surface into the patch.

BRIEF DESCRIPTION OF THE FIGURES

The patent or application file contains at least one drawing executed in color. Copies of this patent or patent application publication with color drawing(s) will be provided by the Office upon request and payment of the necessary fee.

The figures are furnished with the application to understand the invention sought to be patented. It shall not be construed as only way to perform the invention has sought to be patented.

DETAILED DESCRIPTION

Definitions and General Techniques

Figure 1:
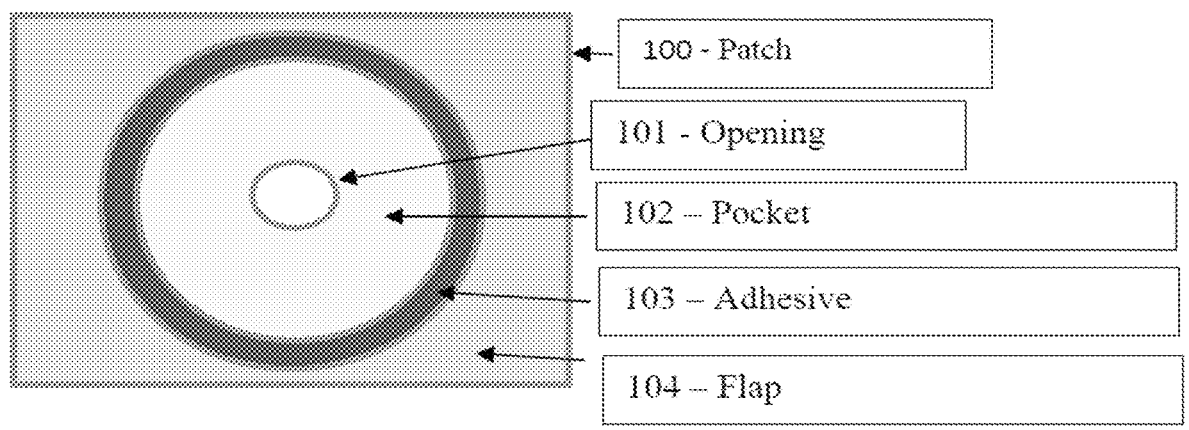
FIG. 1 shows an embodiment a patch (100). The center is the opening (101) of the patch. The area beyond the opening depicts the area where introduced material such as a liquid can be trapped in a pocket (102). Further, the area beyond the opening depicts the adhesive (103) and outside it is the rest of the area of the patch beyond the adhesive referred as a flap (104). A peelable liner (105) is attached as a protective surface.
Figure 2:
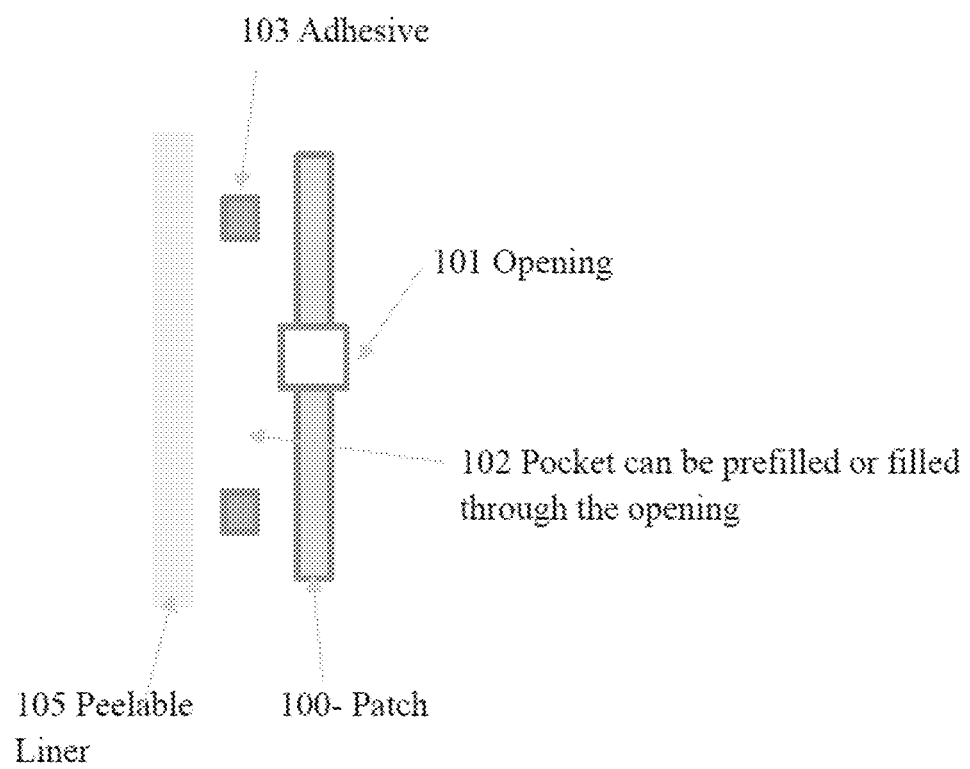
FIG. 2 shows a vertical section of an embodiment of the patch. The first column shows the peelable liner (105), the two boxes after that show the adhesive (103). There is a pocket (102) between these boxes which can be prefilled or filled through the opening (101). The further column is the patch, in there is an opening shown in white box.
Figure 3A:
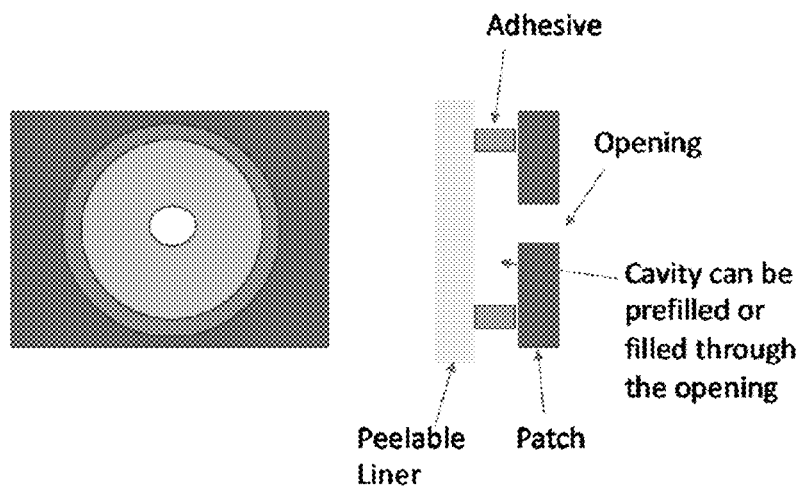
FIG. 3A shows an embodiment of the patch without a tubular structure connected to a patch opening.
Figure 3B:
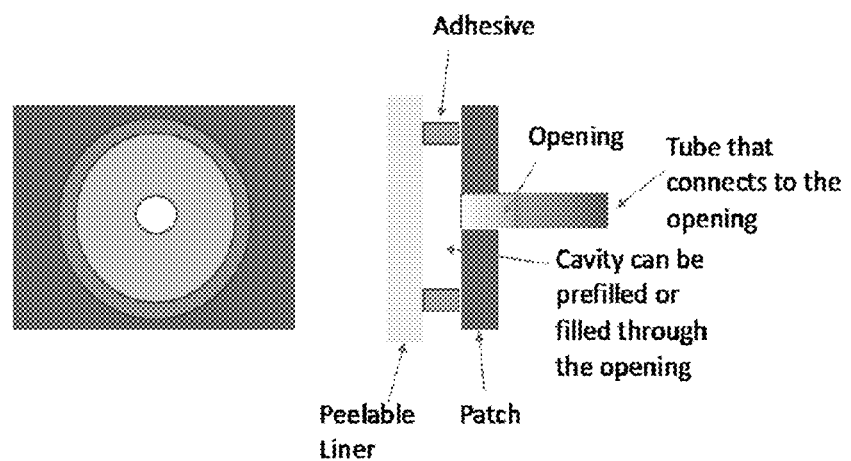
FIG. 3B shows an embodiment of the patch with a tubular structure connected to a patch opening.
Figure 4:
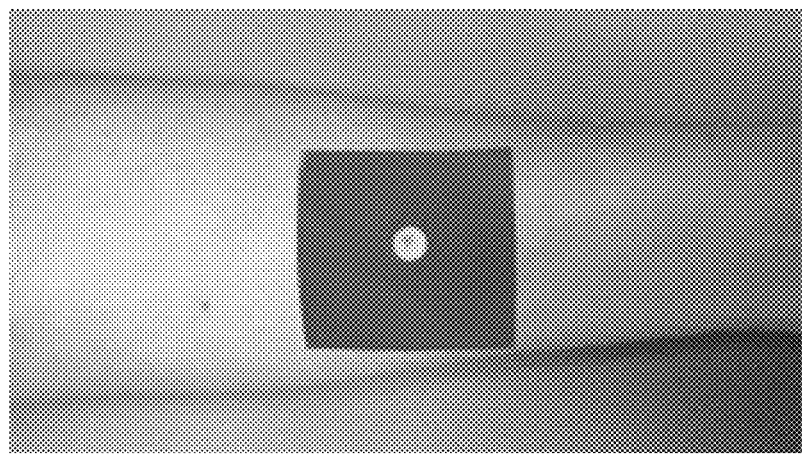
FIG. 4 shows an embodiment of the patch attached to a surface of a skin.

For simplicity and clarity of illustration, the drawing illustrates the general manner of construction. Descriptions and details of well-known features and techniques may be omitted to avoid unnecessarily obscuring the present disclosure. Additionally, elements in the drawing are not necessarily drawn to scale. For example, the dimensions of some of the elements in the figures may be exaggerated, relative to other elements, to help improve the understanding of embodiments of the present disclosure. The same reference numeral in different figures denotes the same element.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include," and "have," and any variations thereof, are intended to cover a non-exclusive inclusion, such that a process, method, system, article, device, or apparatus that comprises a list of elements is not necessarily limited to those elements, but may include other elements not expressly listed or inherent to such process, method, system, article, device, or apparatus.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments of the apparatus, methods, and/or articles of manufacture described herein are, for example, capable of operation in other orientations than those illustrated or otherwise described herein.

No element, act, or instruction used herein should be construed as critical or essential unless explicitly described as such. Also, as used herein, the articles "a" and "an" are intended to include items and may be used interchangeably with "one or more." Furthermore, as used herein, the term "set" is intended to include items (e.g., related items, unrelated items, a combination of related items, and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

The terms "couple," "coupled," "couples," "coupling," and the like should be broadly understood and refer to connecting two or more elements mechanically and/or otherwise. Two or more electrical elements may be electrically coupled together, but not be mechanically or otherwise coupled together. Coupling may be for any length of time, e.g., permanent, or semi-permanent or only for an instant. "Electrical coupling" and the like should be broadly understood and include electrical coupling of all types. The absence of the word "removably," "removable," and the like near the word "coupled," and the like does not mean that the coupling, etc. in question is or is not removable.

As defined herein, two or more elements are "integral" if they are comprised of the same piece of material. As defined herein, two or more elements are "non-integral" if each is comprised of a different piece of material.

As defined herein, "real-time" can, in some embodiments, be defined with respect to operations carried out as soon as practically possible upon occurrence of a triggering event. A triggering event can include receipt of data necessary to execute a task or to otherwise process information. Because of delays inherent in transmission and/or in computing speeds, the term "real time" encompasses operations that occur in "near" real time or somewhat delayed from a triggering event. In a number of embodiments, "real time"

can mean real time less a time delay for processing (e.g., determining) and/or transmitting data. The particular time delay can vary depending on the type and/or amount of the data, the processing speeds of the hardware, the transmission capability of the communication hardware, the transmission distance, etc. However, in many embodiments, the time delay can be less than approximately one second, two seconds, five seconds, or ten seconds.

The present invention may be embodied in other specific forms without departing from its spirit or characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

As defined herein, "approximately" can, in some embodiments, mean within plus or minus ten percent of the stated value. In other embodiments, "approximately" can mean within plus or minus five percent of the stated value. In further embodiments, "approximately" can mean within plus or minus three percent of the stated value. In yet other embodiments, "approximately" can mean within plus or minus one percent of the stated value.

As defined herein, "about" can, in some embodiments, mean within plus or minus five units of the stated value. In other embodiments, "about" can mean within plus or minus three units of the stated value. In further embodiments, "about" can mean within plus or minus two units of the stated value. In yet other embodiments, "about" can mean within plus or minus one unit of the stated value.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, health monitoring described herein are those well-known and commonly used in the art.

The methods and techniques of the present invention are generally performed according to conventional methods well known in the art and as described in various general and more specific references that are cited and discussed throughout the present specification unless otherwise indicated. The nomenclatures used in connection with, and the procedures and techniques of embodiments herein, and other related fields described herein are those well-known and commonly used in the art.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment", or "in an embodiment", or the like, in places throughout the specification are not necessarily all referring to the same embodiment.

Furthermore, the features, structures, or characteristics may be combined in any suitable manner in one or more embodiments. Thus, the features, structures, or characteristics illustrated or described in connection with one embodiment may be combined, in whole or in part, with the features structures, or characteristics of one or more other embodiments without limitation. Such modifications and variations are intended to be included within the scope of the present invention.

The following terms and phrases, unless otherwise indicated, shall be understood to have the following meanings.

The term "Device" is defined by a physical hardware or an equipment or a thing made or adapted for a particular purpose.

In an embodiment, device may be suitable for application to a patient's skin surface. and that includes a transdermal device for introducing fluid through the patient's skin. In certain embodiments, such a device may comprise a reservoir containing a fluid medicament and a release means for releasing the fluid medicament from the reservoir through the transdermal device into the patient's skin.

In an embodiment, device can be a medical device. A medical device can be any instrument, apparatus, implement, machine, appliance, implant, reagent for in vitro use of material or other similar or related article, intended by the manufacturer to be used, alone or in combination for a medical purpose.

In an embodiment, a device may include a percutaneous device unit and a reservoir unit, the percutaneous device unit of the device comprising a transdermal device and a mounting surface for application to a patient's skin. The reservoir unit comprises a reservoir containing a fluid medicament and a release assembly for cooperating with the reservoir to release the fluid medicament from the reservoir through the transdermal device into the patient's skin. The percutaneous device unit and the reservoir unit can also be secured to each other in use to allow fluid to flow between the reservoir and the percutaneous device. The percutaneous device unit and the reservoir unit comprise releasable coupling means that allow the reservoir unit to be secured to the percutaneous device unit in use. Such a medical device comprising two units is also considered a medical system. Each of the percutaneous device unit and the reservoir unit each include a percutaneous device and a housing in which the reservoir and release assembly are disposed. The term "release assembly" includes a collection of components or structures that together allow the liquid to be released from the reservoir. The discharge assembly can be, for example, a mechanical pump (eg, membrane pump, piston pump or roller pump), mechanically driven pump (eg, spring driven), gas driven pump, or osmotic engine driven pump combined with electronically controlled actuation. The discharge assembly can also be in the form of a collection of components or structures that collectively release fluid from the reservoir when controlled or actuated by a controller external to the assembly.

In an embodiment, the device may include an image guided robotic device to perform a diagnostic or therapeutic medical procedure. In one embodiment, the robotic device includes an imaging machine, an actuator, and a controller for controlling the actuator. The robotic device may be configured to introduce a tubular shaped device such as a needle, a catheter, or a cannula into an anatomical structure of a human body. The device and its components may be sized for use as a portable device and/or operable using one hand of the operator. The anatomical structure may be any portion of the body of diagnostic or therapeutic interest.

In an embodiment, the device may be in the form of patch having a number of projections provided on a surface of a substrate. The projections and substrate may be formed from any suitable material, but in one example, are formed from a silicon type material, allowing the device to be fabricated using processes such as vapour deposition, silicon etching, Deep Reactive Ion Etching (DRIE), or the like. The projections may be typically solid, non-porous and non-hollow, although this is not essential.

The term "Patch" is defined by a substrate marked out from the rest by a particular characteristic.

In an embodiment, the patch may include microneedles. Micro-needle refers to a needle of several hundred micrometers in size and can deliver drugs directly through the stratum corneum of the skin. Micro needles are manufactured using a variety of materials including metals, glass, silicon and polymers. The microneedle patch comprises: a flat patch layer; and a microneedle arranged on one surface of the patch layer, including air-pocket therein, and formed as a polymer having at least one of swelling properties and solubility. The term "microneedles" has a plurality of protrusions, and have a height (h), measured from the inner surface of the intermediate layer, or the inner surface of the substrate layer, if present, to the tip of the microneedle, of about 100 µm-1,500 µm, including for example about 300 µm-1,000 µm, or about 400 µm-800 µm, including about 100 µm, 200 µm, 300 µm, 400 µm, 500 µm, 600 µm, 700 µm, 800 µm, 900 µm, 1,000 µm, 1,100 µm, 1,200 µm, 1,300 µm, 1,400 µm, and 1,500 µm. In other embodiments, the aspect ratio (i.e., ratio of height to base) of the microneedles is about 1.0-4.0, including about 1.5-3.5, and 2.0-3.0, including, for example, about 1.0, 1.25, 1.5, 1.75, 2.0, 2.25, 2.5, 2.75, 3.0, 3.25, 3.5, 3.75, and 4.0. In some embodiments, the microneedles have absolute dimension for the base of about 50 µm, 100 µm, 150 µm, 200 µm, 250 µm, 300 µm, 350 µm, 400 µm, 450 µm, 500 µm, 550 µm, or 600 µm. In other embodiments, the microneedles have an absolute dimension (height to base) of about 400:200 µm, 600:300 µm, or 800:400 µm. Microneedles may be formed into any suitable shape including, for example, conical, diamond, tetrahedral, and pyramidal shapes.

In an embodiment, the patch may be a transdermal patch. The term "transdermal" is a route of administration wherein ingredients are delivered across the skin for systemic distribution. Examples include transdermal patches used for medicine delivery. The drug is administered in the form of a patch or ointment that delivers the drug into the circulation for systemic effect. Transdermal administration can be accomplished by applying, pasting, rolling, attaching, pouring, pressing, rubbing, etc., of a transdermal preparation onto a skin surface. The term "transdermal patch" refers to a matrix or liquid reservoir type of delivery device which is used to transdermally deliver doses of a substance, over a specific application period.

In an embodiment, the patch can be a peelable pouch, including a substantially flat enclosure formed by a first and a second opposing flexible plies. A seal can extend along at least a portion of a perimeter of the opposing plies. A flat, flexible transdermal patch can be disposed in the enclosure, the patch including a bioactive agent dissolved in a layer of adhesive. A release liner can be removably attached over the layer of adhesive. The patch and the release liner can together be sufficiently resilient so as to generate a spring force when displaced out of the flat configuration. The first and the second plies can each be separable along the seal and can be displaceable out of the flat configuration. The spring force generated by the patch and the release liner can be sufficient to overcome an adhesive force created by the adhesive between the patch and one of the plies.

In an embodiment, a patch may be typically a small adhesive bandage that contains the drug to be delivered and these bandages can take several forms. The simplest type is an adhesive monolith comprising a drug-containing reservoir disposed on a backing. The reservoir is typically formed from a pharmaceutically acceptable pressure sensitive adhesive but, in some cases, can be formed from a non-adhesive material, the skin-contacting surface of which is provided with a thin layer of a suitable adhesive. The rate at which the drug is administered to the patient from these patches can vary due to normal person-to-person and skin site-to-skin site variations in the permeability of skin to the drug.

In an embodiment, patch may be a silicon patch, wherein silicon patch may be called as silicone gel sheeting. It may also be known as medical patch or medical silicone patch. Medical silicone patch includes a silicone rubber layer, a silicone gel layer and a release film, a silicone gel layer containing essential oils O-cyclodextrin inclusion particles. Essential oils O-cyclodextrin as the essential oil is lavender essential oil or essential oil. Further, along with essential oils from a β-cyclodextrin inclusion particles and hydrogenated silicone oil, vinyl silicone oil can be chosen.

In an embodiment, patch may include a flexible backing, and a base layer laminated on the backing. Herein, the patch of the present invention is principally for application to skin, and may include plasters, cataplasms, tapes, adhesive plasters, sheets, wound dressings, cosmetic facial masks, tapes made by 3M® and the like. The base layer of patch may include a SIS block copolymer as an essential component, and preferably, further includes a tackifier and a plasticizer.

In an embodiment, the patch may also have a plurality of projections urged against a subject's skin shown generally, so that the projections pierce the stratum corneum, and enter the epidermis to reach targets of interest. The projection includes a targeting section, intended to deliver the material or stimulus to targets within the body, and a support section for supporting the targeting section.

In an embodiment, patches may be multi-layer laminate or liquid reservoir type patches in which a drug release rate controlling membrane is disposed between the drug reservoir and the skin contact adhesive. This membrane serves to reduce the effect of fluctuations in skin permeability by reducing the in vitro release rate of the drug from the patch. This type of patch is generally preferred when a significantly more potent drug is administered, but to achieve a similar rate of drug delivery, it usually has to cover a larger area of skin than a monolithic patch.

The term "adhesive" is any non-metallic substance applied to one or both surfaces of two separate items that binds them together and resists their separation. Adhesive, also known as glue, cement, mucilage, or paste. There are a large number of adhesive types for various applications. They may be classified in a variety of ways depending on their chemistries (e.g. epoxies, polyurethanes, polyimides), their form (e.g. paste, liquid, film, pellets, tape), their type (e.g. hot melt, reactive hot melt, thermosetting, pressure sensitive, contact, etc.), or their load carrying capability (structural, semi-structural, or non-structural). Any type of adhesive comes under the scope of the invention. There are adhesives known in the art based on their functionality namely core adhesives add strength to the diaper pad when it is wet; construction adhesives bind the waterproof backsheet to the nonwoven absorbent pads; and elastic adhesives bind legs, waist and lateral panel sheets.

In an embodiment, adhesive is disposed on a backing. The backing may be removable (such as a release liner, including a microstructured release liner or a carrier film) or non-removable such as a polymeric film or a rigid or non-rigid substrate.

In an embodiment, pressure sensitive adhesive (PSA) compositions are well known to those of ordinary skill in the art to possess properties including (1) aggressive and permanent tack, (2) adherence with no more than finger pressure, (3) sufficient ability to hold onto an adherend, and (4) sufficient cohesive strength. Materials that have been found to function well as PSAs include polymers designed and formulated to exhibit the requisite viscoelastic properties resulting in a desired balance of tack, peel adhesion, and shear holding power. The pressure sensitive adhesives are crosslinked prior to embossing. Examples of suitable adhesives include crosslinked acrylics, rubbers, thermoplastic elastomers, silicones, and the like.

In an embodiment, adhesive may be "hot melt adhesive". Hot melt adhesive refers to an article that is solid at room temperature, melts into a liquid by heating, and can achieve adhesion when cooled by applying pressure for several minutes and is to be applied It means an adhesive such as polyolefin block copolymer (SBS, SIS), ethylene vinyl acetate copolymer (EVA) or the like, which is coated thereon.

In an embodiment, adhesive may be "structural adhesive". The structural adhesive is a structure intended to withstand strong forces with high strength, relatively high yield strength, aging resistance, fatigue resistance, corrosion resistance, and stable performance during a specified lifetime. It means an adhesive such as epoxy resin and polyurethane that can be applied to body adhesion.

In an embodiment, the pressure sensitive adhesive is based on at least one poly(meth)acrylate (i.e., a (meth) acrylic pressure sensitive adhesive). Particularly preferred poly(meth)acrylates are derived from: (A) at least one monoethylenically unsaturated alkyl (meth) acrylate monomer (i.e., alkyl acrylate and alkyl methacrylate monomer); and (B) at least one monoethylenically unsaturated free-radically copolymerizable reinforcing monomer. The reinforcing monomer has a homopolymer glass transition temperature (Tg) higher than that of the alkyl (meth)acrylate monomer and is one that increases the glass transition temperature and cohesive strength of the resultant copolymer. Herein, "copolymer" refers to polymers containing two or more different monomers, including terpolymers, tetrapolymers, etc.

In one embodiment, adhesives can be coated using a solvent-based method. For example, the adhesive can be coated by such methods as knife coating, roll coating, gravure coating, rod coating, curtain coating, and air knife coating. The adhesive mixture may also be printed by known methods such as screen printing or inkjet printing. The coated solvent-based adhesive is then dried to remove the solvent. Typically, the coated solvent-based adhesive is subjected to elevated temperatures, such as those supplied by an oven, to expedite drying of the adhesive.

In one embodiment, the thickness of the adhesive layer may be at least about 1 micrometer, at least 5 micrometers, at least 10 micrometers, at least 15 micrometers, or at least 20 micrometers. The thickness is often no greater than about 200 micrometers, no greater than about 175 micrometers, no greater than about 150 micrometers, or no greater than about 125 micrometers. For example, the thickness can be 1 to 200 micrometers, 5 to 100 micrometers, 10 to 50 micrometers, 20 to 50 micrometers, or 1 to 15 micrometers.

In one embodiment, the adhesives may be self-wetting and removable. The adhesives exhibit great conformability permitting them to spontaneously wet out substrates. The surface characteristics also permit the adhesives to be bonded and removed from the substrate repeatedly for repositioning or reworking. The strong cohesive strength of the adhesives gives them structural integrity limiting cold flow and giving elevated temperature resistance in addition to permanent removability.

In one embodiment, adhesives may be viscoelastic or elastomeric adhesives, rubber-based adhesives, silicon-based adhesives. Viscoelastic or elastomeric adhesives further include elastomeric polyurethane or silicone adhesives and the viscoelastic optically clear adhesives CEF22, 817x, and 818x, all available from 3M Company, St. Paul, Minn. Other useful viscoelastic or elastomeric adhesives include PSAs based on styrene block copolymers, (meth)acrylic block copolymers, polyvinyl ethers, polyolefins, and poly (meth)acrylates.

In an embodiment, adhesive may include tackifier not particularly limited, and for example, alicyclic saturated hydrocarbon resins (synthetic petroleum resin) as well as rosin ester derivatives, terpene-based resins, phenolic resins and the like are preferred. The content of the tackifier is not particularly limited and is preferably 10 to 35% by weight based on the weight of the entire base. When the content of the tackifier is too low, the adhesion becomes insufficient. In contrast, when the content of the tackifier is too high, the adhesion becomes excessively great, thus a user may experience excessive pain when a skin patch is peeled from the skin.

In an embodiment, adhesives may have a microreplicated topography are prepared from contacting a microembossed pattern to a layer of adhesive. When an adhesion interface is established between the layer of adhesive and a supporting substrate, the topography of the adhesive surface controls the performance of the adhesion interface. Articles having microreplicated adhesive surfaces are also disclosed that have an advantage of providing microchannels for fluid egress for an effective period of time. Multiple microembossed patterns produce microreplicated adhesive surfaces having both microchannels for fluid egress and pegs for improved adhesive properties.

The term "Skin": is the layer of usually soft, flexible outer tissue covering the body of a vertebrate or invertebrate animal, with three main functions: protection, regulation, and sensation. It also means the outermost protective covering composed of cells such as keratinocytes, fibroblasts and melanocytes. Skin includes an outer epidermal layer and an underlying dermal layer. Skin may also include hair and nails as well as other types of cells commonly associated with skin, such as, for example, myocytes, Merkel cells, Langerhans cells, macrophages, stem cells, sebocytes, nerve cells and adipocytes.

In an embodiment, the skin is human skin. The human skin is the outer covering of the body and is the largest organ of the integumentary system. The skin has up to seven layers of ectodermal tissue and guards the underlying muscles, bones, ligaments and internal organs. Skin is composed of three primary layers: the epidermis, the dermis and the hypodermis. Skin has mesodermal cells, pigmentation, such as melanin provided by melanocytes, which absorb some of the potentially dangerous ultraviolet radiation (UV) in sunlight. It also contains DNA repair enzymes that help reverse UV damage, such that people lacking the genes for these enzymes suffer high rates of skin cancer. One form predominantly produced by UV light, malignant melanoma, is particularly invasive, causing it to spread quickly, and can often be deadly. Human skin pigmentation varies among populations in a striking manner. This has led to the classification of people(s) on the basis of skin colour. In terms of surface area, the skin is the second largest organ in the human body (the inside of the small intestine is 15 to 20 times larger). For the average adult human, the skin has a surface area of between 1.5-2.0 square metres (16-22 sq ft). The thickness of the skin varies considerably over all parts of the body, and between men and women and the young and the old. An example is the skin on the forearm which is on average 1.3 mm in the male and 1.26 mm in the female. The average human skin cell is about 30 micrometres (μm) in diameter, but there are variants. A skin cell usually ranges from 25-40 μm2, depending on a variety of factors.

In an embodiment, skin is a complex structure that functions as a barrier to ingress of foreign substances into the body. Molecules moving from the environment into and through intact skin must first penetrate the stratum corneum, which presents the primary barrier to absorption of topical compositions or transdermally administered drugs, especially for oil-insoluble and ionized salt forms of drugs.

Pocket: is a pouch or a small recess to hold a material.

In an embodiment, a patch can have one or plurality of pockets.

In an embodiment, pocket is preferably made by overlaying in the form of a bag or flat sections of substrate matrix, in particular sections of the film, or by bending the portion of the film that is part of the lining on the patch.

In an embodiment, pocket is the recess between the patch and the skin. This allows introduction of a material into the pocket, and to hold the material within the pocket.

In an embodiment, pocket is the recess between the patch and the peelable liner.

In an embodiment, the pocket comprises a space or a pattern.

In an embodiment, pockets may be open not essentially toward the center of the patch to facilitate introduction of material inside the pocket. The depth of said at least one pocket is preferably within in a range, wherein the lower limit of range is selected from 0.5 cm, 1 cm, 1.5 cm, 2 cm, 2.5 cm, 3 cm, 3.5 cm, 4, 5 cm and wherein the upper limit of range is selected from 7 cm, 8 cm, 9 cm, 10 cm, 11 cm, 12 cm, 13 cm, 14 cm and 15 cm.

In an embodiment, the pocket with opening may have a flap to close to close such openings.

In an embodiment, the material may include drug with or without excipient.

The term "Drug" as used herein is generally meant to refer to any substance that alters the physiology of an animal. The term "drug" may be used interchangeably herein with the terms "therapeutic agent", "medication", "pharmacologically active agent" and the like. It will be understood that a "drug" formulation may include more than one therapeutic agent, wherein exemplary combinations of therapeutic agents include a combination of two or more drugs.

By way of example, and not limitation, drug substances suitable for use in the present invention include physiologically active peptides and/or proteins, antineoplastic agents, antibiotics, analgesics, anti-inflammatory agents, muscle relaxants, anti-epileptics, anti-ulcerative agents, anti-allergic agents, cardiotonics, anti-arrhythmic agents, vasodilators, antihypertensive agents, antidiabetic agents, anti-hyperlipidemics, anticoagulants, hemolytic agents, antituberculous agents, hormones, narcotic antagonists, osteoclastic suppressants, osteogenic promoters, angiogenesis suppressors, and various mixtures, salts, prodrugs and co-drugs thereof.

In an embodiment, physiologically active peptides and/or proteins range in molecular weight front 200 to 100,000 and include but are not limited to human growth hormone, growth hormone releasing hormone, growth hormone releasing peptide, interferons, colony stimulating factors, interleukins, macrophage activating factors, macrophage peptide, B-cell factors, T-cell factors, protein A, allergy repressors, immunotoxins, lymphotoxins, tumor necrosis factors, tumor repression factors, vascular endothelial growth factor (VEGF), fibroblast growth factor (FGF), metastasis growth factors, alpha-1 antitrypsin, apolipoprotein-E, erythropoietin, Factor VII, Factor VIII, Factor IX, plasminogen activating factors, urokinase, streptokinase, Protein C, C-reactive protein, superoxide dismutase, platelet-derived growth factors, epidermal growth factors, osteogenic growth factors, osteogenesis-promoting proteins, calcitonin, insulin, atriopeptin, cartilage induction factors, connective tissue activating factors, follicle stimulating hormone, leutenizing hormone, leutenizing hormone releasing hormone, nerve growth factors, parathyroid hormone, relaxin, secretin, somatomedin, insulin-like growth factors, adrenocorticotropic hormone, glucagons, cholecystokinin, pancreatic polypeptides, gastrin releasing hormone, coticotropin releasing factors, thyroid stimulating hormones, mono- and poly-clonal antibodies, vaccines, and mixtures thereof. Pegylated versions of proteins, peptides, or other biologic response modifiers are also suitable for incorporation into the compositions of the present invention.

In an embodiment, antiproliferative/antimitotic drugs and prodrugs include natural products such as vinca alkaloids (e.g., vinblastine, vincristine, and vinorelbine), paclitaxel, epidipodophyllotoxins (e.g., etoposide, teniposide), antibiotics (e.g., actinomycins, daunorubicin, doxorubicin and idarubicin), anthracyclines, mitoxantrone, bleomycins, plicamycin (mithramycin) and mitomycin, enzymes (e.g., L-asparaginase); antiplatelet prodrugs; antiproliferative/antimitotic alkylating prodrugs such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), triazenes, dacarbazine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine (cladribine); platinum coordination complexes (cisplatin, carboplatin), procarbazine, hydroxyurea, mitotane, aminoglutethimide; hormones (e.g., estrogen, progestin); anticoagulants (e.g., heparin, synthetic heparin salts and other inhibitors of thrombin); fibrinolytic prodrugs such as tissue plasminogen activator, streptokinase and urokinase, aspirin, dipyridamole, ticlopidine, clopidogrel, abciximab; antimigratory; antisecretory (breveldin); anti-inflammatory agents such as corticosteroids (cortisol, cortisone, fludrocortisone, flucinolone, prednisone, prednisolone, methylprednisolone, triamcinolone, betamethasone, and dexamethasone), NSAIDS (salicylic acid and derivatives, aspirin, acetaminophen, indole and indene acetic acids (indomethacin, sulindac and etodalac), heteroaryl acetic acids (tolmetin, diclofenac, and ketorolac), arylpropionic acids (e.g., ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives (e.g., cyclosporine, tacrolimus (FK-506), sirolimus (rapamycin), azathioprine, and mycophenolate mofetil); angiogenic agents such as vascular endothelial growth factor (VEGF), fibroblast growth factor (FGF); angiotensin receptor blocker; nitric oxide donors; anti-sense oligionucleotides and combinations thereof; cell cycle inhibitors, mTOR inhibitors, and growth factor signal transduction kinase inhibitors.

In an embodiment, the drug substance is a prodrug or co-drug of an opioid analgesic or an opioid antagonist. Exemplary opioids include morphine and morphine derivatives, such as apomorphine, buprenorphine, codeine, dihydrocodeine, dihydroetorphine, diprenorphine, etorphine, hydrocodone, hydromorphone, levorphanol, meperidine, metopon, o-methylnaltrexone, naloxone, naltrexone, normorphine, oxycodone, and oxymorphone. In other embodiments, the opiod is fentanyl or a fentanyl derivative which can be derivatized to form a prodrug or co-drug, such as beta-hydroxy-3-methylfentanyl. The drug substances may optionally be in pharmaceutically acceptable salt forms.

In an embodiment, drug may be an anti-oxidizing agent is not particularly limited, and for example, dibutylhydroxytoluene, ascorbic acid, tocopherol, tocopherol ester derivatives, butylhydroxyanisole, 2-mercaptobenzimidazole, and the like.

In an embodiment, the excipient is not particularly limited, and examples thereof include silicon compounds such as silicate anhydride, light silicate anhydride and hydrous silicic acid, cellulose derivatives such as ethyl cellulose, methyl cellulose, hydroxypropyl cellulose and hydroxypropylmethyl cellulose, water soluble polymers such as polyvinylalcohol, aluminum compounds such as dry aluminum hydroxide gel and hydrous aluminum silicate, kaolin, titanium oxide, and the like.

In an embodiment, material may include solubilizer, and the transdermal absorption promoting agent.

The term "transdermal absorption promoting agent" may also be interchangeably called as "percutaneous penetration enhancer" or "penetration enhancer". They are also called as enhancer or accelerators. Penetration enhancer are chemical enhancers that help in absorption of co-administered moieties or drug substance to improve solubility within the stratum corneum. The penetration enhancers are believed to operate mainly in the intercellular spaces of the stratum corneum.

In an embodiment, penetration enhancer for example but not limited to triacetin, crotamiton, cetyl lactate, diisopropyl adipate, oleic acid, and oleyl alcohol, polyhydric alcohols such as polyethylene glycol (average molecular weight: 200 to 30000), glycerin, ethylene glycol, and diethylene glycol, fatty acids such as oleic acid, isostearic acid and citric acid, fatty acid esters such as isopropyl myristate, isopropyl palmitate, and diisopropyl adipate, fatty acid polyhydric alcohol esters such as caprylic acid monoglyceride, caprylic acid triglyceride, and sorbitan fatty acid esters, terpenes such as menthol, menthol derivatives, peppermint oil, and limonene, N-methyl-2-pyrrolidone, crotamiton, polyvinylalcohol, and the like are exemplified. Penetration enhancer may also include benzyl alcohol, propylene glycol monolaurate and a $C2$-$C_6$ alkanediol, 1.2-propylene glycol, dipropylene glycol, hexylene glycol, isoparaffin, sodium laurylsulfate, ethylene oxide adducts of lauryl alcohol, fatty acids, ethyl alcohol, polyethylene glycol fatty acid esters, glycerol, polyoxyethylene sorbitan fatty acid esters, propyl carbonate, sodium pyrrolidonecarboxylate, urea, lactic acid, sodium lactate, lecithin, dimethyl sulfoxide, pyrrolidonecarboxylate, nicotinate, N-methylproline ester, amine oxide and other ingredients are prepared for external application as a transdermal absorption enhancer or penetration enhancer.

In an embodiment, material may include solubility controlling agent, for example but not limited to a salt.

In an embodiment, material may include pH controlling agent.

In an embodiment, material may include imaging agent. Suitable Imaging agent with vehicle is radioactive iodine, or as a radioactive metal chelate complex of a compound of formula (Ia) and/or (Ib), a radioisotope (e.g., 18F) or like.

The term "surface tension" is the tendency of liquid surfaces to shrink into the minimum surface area possible. Surface tension is caused by the effects of intermolecular forces at the interface. Surface tension depends on the nature of the liquid, the surrounding environment and temperature. Its units are Newton/meter.

In an embodiment, surface tension in patch block opening using the from the hydrophilic component. The surface tension generally can cause surface sealed with insufficient pore structure. It is believed that surface tension can further the key element in the patch block each other, thereby make this compact structurization and seal in the method a patch would block holes.

In an embodiment, due to surface tension, the pocket is able to hold the material within the pocket.

In an embodiment, the flap comprises a net structure to hold a surface tension of a liquid.

In an embodiment, the material held inside the pocket has a surface tension to be able to be held within the pocket.

In an embodiment, the surface tension of the liquid is 1 nN/m, 2 nN/m, 3 nN/m, 5 nN/m and so on, 1 µN/m, 2 µN/m, 3 µN/m, 5 µN/m and so on, 1 mN/m, 2 mN/m, 3 mN/m, 5 mN/m and so on.

The term "Permeable" refers to a membrane that permit liquids or gases to pass through. Permeable membrane has pores. The rate of flow of liquid through a porous body is proportional to the pressure gradient in the pores. To measure the permeability, a pressure differential is applied across a layer of porous material and the rate of flow is measured. The permeability is measured in cm/s. In other words the permeable material may refer to any material into which additional species (such as atoms, molecules, or ions) may be introduced.

The term "Non-permeable" refers to a substance or material that does not allow water or liquid to pass through it.

In an embodiment, in the present invention patch is permeable or non-permeable to any liquid or gas or selectively to a solid, without any external driving force.

In an embodiment, the permeable or non-permeable also in context of skin permeability or non-permeability to a liquid or gas or selectively to a solid, when administered through the patch. The rate at which the drug is administered to the patient from these patches can vary due to normal person-to-person and skin site-to-skin site variations in the permeability of skin to the drug.

In an embodiment, the substrate comprises a non-permeable material and/or a permeable material. In an embodiment, the substrate is gas permeable liquid nonpermeable; gas permeable liquid permeable; gas nonpermeable liquid permeable; gas non-permeable, liquid nonpermeable; or selectively permeable and can be solid permeable or non-permeable also.

In an embodiment, the selectively to a solid means when the size of the solid is less than 1 mm. The solid can be of size 1 Ao, 2 Ao, 3 Ao, 5 Ao, 1 nm, 2 nm, 3 nm or 5 nm, 1 µm, 2 µm, 3 µm, 5 µm or 1 mm.

In an embodiment, the substrate or the flap is permeable or non-permeable.

In an embodiment, a membrane or material is permeable or non-permeable when used passively.

In an embodiment, a membrane or material is permeable or non-permeable when used actively.

The term "Membrane" refers to a pliable sheet forming a barrier, boundary, partition, or lining. In an embodiment, membrane is a matrix comprising a polymer substrate. In one embodiment, polymer substrate includes single polymers. In a particular embodiment, the polymer is selected from insoluble polymer or water soluble polymer. Ethane-acetic acid ethyenyl ester and ethyl cellulose are typical insoluble polymers. Polyvinyl alcohol is typical water-soluble polymer.

In an embodiment, the polymer substrate includes two or more polymer. In one embodiment, described two or more polymer are selected from insoluble polymer, water-soluble polymer or combinations thereof. In a particular embodiment, the polymer substrate includes ethane-acetic acid ethyenyl ester and ethyl cellulose. In another specific implementation, the polymer substrate includes ethane-acetic acid ethyenyl ester and polyvinyl alcohol.

In an embodiment, the membrane is of skin or human skin or the substrate or the flap or the patch or the device in the whole or the imaging instrument.

In an embodiment, the membrane is biological or non-biological or natural or synthetic or semi-synthetic.

In an embodiment, Biological membranes include cell membranes (outer coverings of cells or organelles that allow passage of certain constituents); nuclear membranes, which cover a cell nucleus; and tissue membranes, such as mucosae and serosae. Synthetic membranes are made by humans for use in laboratories and industry. Semi-synthetic membrane contains both natural as well as non-natural means.

In an embodiment, degree of selectivity of a membrane depends on the membrane pore size. Depending on the pore size, they can be classified as microfiltration (MF), ultrafiltration (UF), nanofiltration (NF) and reverse osmosis (RO) membranes.

In an embodiment, membranes can also be of various thickness, with homogeneous or heterogeneous structure. Membranes can be neutral or charged, and particle transport can be active or passive. The latter can be facilitated by pressure, concentration, chemical or electrical gradients of the membrane process.

In an embodiment, membrane may be formed of a polymer having at least one of swelling property and solubility. Swellability refers to the property of increasing the volume by absorbing a liquid such as water. In the present invention, "swelling polymer" means a polymer showing swelling property as a main property and does not mean that the swelling polymer of the present invention does not have other properties such as solubility other than swelling property. That is, the swellable polymer of the present invention has swellability as a main property and can exhibit other properties. For example, the swellable polymer of the present invention can exhibit swelling property and solubility simultaneously. The term "soluble polymer" in the present invention means a polymer having solubility as a main property, which is a property dissolved in a solvent. As described above, the soluble polymer of the present invention may exhibit properties other than solubility. For example, the soluble polymer may exhibit both solubility and swelling properties. The polymer of the present invention may be a polymer capable of dissolving by a body fluid, or may be a biodegradable polymer that can be decomposed by body fluids, enzymes, microorganisms, or the like in vivo. In addition, the polymer may be a biocompatible polymer having no toxicity to the human body and suitable for application to living bodies. For example, the polymer may be selected from the group consisting of hyaluronic acid, alginic acid, pectin, carrageenan, chondroitin (sulfate), dextran (sulfate), chitosan, polylysine, collagen, gelatin, carboxymethyl chitin, fibrin, agarose, pullulan, cellulose, polyethylene oxide, poly (N-) isopropylacrylamide (PNIPAAm), polyacrylamide (PAAm), polymethacrylic acid, polymaleic acid, polyvinylalcohol, Poly (methyl methacrylate) (MMA-co-HEMA) (poly (methyl methacrylate)), polyethylene oxide (PEO) (co-hydroxylethyl methacrylate)), poly (acrylonitrile-aryl sulfonate), poly (glucosyloxyethyl methacrylate-sulfate) (P (GEMA (glucosyloxyethyl methacrylate) Oxide (PEO)-poly (PEO-PPO-PEO) terpolymer, a polyethylene oxide-polypropylene oxide-polyethylene oxide (PEO-PPO-PEO) terpolymer, N-carboxyanhydride, polystyrene, and copolymers of monomers that form such a polymer Or more.

Biocompatible: Biocompatibility is related to the behavior of biomaterials in various contexts. The term refers to the ability of a material to perform with an appropriate host response in a specific situation. The immune response and repair functions in the body are so complicated it is not adequate to describe the biocompatibility of a single material in relation to a single cell type or tissue. Sometimes biocompatibility testing that is a large battery of in vitro test is used in accordance with ISO 10993 (or other similar standards) to determine if a certain material (or rather biomedical product) is biocompatible. These tests constitute an important step towards the animal testing and finally clinical trials that will determine the biocompatibility of the material in a given application, and thus medical devices such as implants or drug delivery devices.

In an embodiment, the substrate and adhesive in the present invention are biocompatible.

Biocompatible substrate and adhesive can be organic as well as inorganic. Organic adhesive can be from natural or non-natural sources, natural sources included vegetable starch (dextrin), natural resins or animals (e.g. the milk protein casein and hide based animal glues). Inorganic adhesives include non-carbon based adhesives such as cement and mortar.

few examples of biocompatible substrates but not limited are Polydimethylsiloxane (PDMS), Polylactic acid, poly-ε-caprolactone (PCL) film, triglycidylamine. Biocompatible adhesive can be made up of epoxyamine.

In one embodiment of the invention, the substrate is a polymeric substrate.

In one embodiment, the substrate is selected from the group consisting of: latex, vinyl, polymer containing vinyl groups, polyurethane urea, silicone, polyvinyl chloride, polypropylene, styrene, polyurethane, polyester, ethylene vinyl acetate copolymerisate. Polystyrene, polycarbonate, polyethylene, polyacrylate, polymethacrylate, acrylonitrile butadiene styrene, polyamide, and polyimide, or mixtures thereof. In another aspect of the invention, the substrate is selected from the group consisting of natural polymers, degradable polymers, edible polymers, biodegradable polymers, environmentally friendly polymers, and medical grade polymers.

Flexible refers to susceptible to modification or adaptation.

In an embodiment, the patch is flexible. The patch may include a flexible backing, and a base layer laminated on the backing. In an embodiment, the substrate is flexible. The patch on the body surface such that the flexible substrate conforms to the body surface.

In an embodiment, the flexible patch may be flexible, stretchable and breathable to improve patient comfort during use. The fabric of the flexible patch may be rolled, crumpled and folded without compromising its functionality. The flexible patch may be configured or coated to be fire resistant, water resistant or waterproof.

In an embodiment, flexible substrate can be formed of a stretchable material to allow the flexible substrate to conform to a head body surface. According to some embodiments, the flexible substrate has a thickness in the range of from about 0.001 to 0.100 inches. According to some embodiments, the flexible substrate is a substrate material selected from the group consisting of polyvinyl, PET, silicone, polyethylene, polyurethane, and polyamide Compatible: In an embodiment, the compatible is defined as suitable to be used together, or to live or exist together or in harmony. In another embodiment, a material is said to be a compatible when it possesses stability when mixed with another material. This property is called as compatibility. If two materials mix and undergo a chemical reaction, they are considered incompatible. However, if these do not undergo a chemical reaction, it is known as compatible. For example, when stirring a chemical, the stirrer must be stable in the chemical that is being stirred. An example of incompatible is: bleach and ammonia, both commonly used as cleaners can undergo a dangerous chemical reaction when combined with each other. Even though each of them has a similar use, care must be taken not to allows these chemicals to mix.

In an embodiment in the present invention, the compatible preferably is defined as a material which does not undergo chemical reaction, when mixed with material or materials.

In an embodiment, the substrate and the adhesive are compatible with a penetration enhancer.

In an embodiment, the device or the patch is compatible with the skin. That is no adverse reaction take place when the patch is applied on the skin.

Skin-substance: It is defined broadly as any bio-chemical entity existing or present inside a body of human, animal or any organism on which the present invention is intended to work upon. For example but not limited to include Alpha-1 anti-trypsin, Anti-Angiogenesis agents, Antisense, butorphanol, Calcitonin and analogs, Ceredase, chemokines, chemoattractants, chemokinetic agents, COX-II inhibitors, dermatological agents, dihydroergotamine, Dopamine agonists and antagonists, Enkephalins and other opioid peptides, Epidermal growth factors, Erythropoietin and analogs, Follicle stimulating hormone, G-CSF, Glucagon, GM-CSF, granisetron, Growth hormone and analogs (including growth hormone releasing hormone), Growth hormones, irudin and Hirudin analogs such as hirulog, IgE suppressors, Insulin, insulinotropin and analogs, Insulin-like growth factors, Interferons, Interleukins, Luteinizing hormone, Luteinizing hormone releasing hormone and analogs, Low molecular weight heparin, M-CSF, metoclopramide, Midazolam, antibodies, Oligosaccharides, ondansetron, Parathyroid hormone and analogs, Parathyroid hormone antagonists, Prostaglandin antagonists, Prostaglandins, Receptor agonists and antagonists, Recombinant soluble receptors, scopolamine, Serotonin agonists and antagonists, Sildenafil, Terbutaline, Thrombolytics, Tissue plasminogen activators, TNFα, and TNFα antagonist, protein, peptide and polysacchraride, polysaccharide conjugates, toxoids, genetic based vaccines, live attenuated, reassortant, inactivated, whole cells, viruses, bacteria, viral and bacterial vectors including but not limited to those derived from adenoviruses, retroviruses and alpha-viruses) in connection with, addiction, arthritis, cholera, cocaine addiction, diphtheria, tetanus, HIB, Lyme disease, meningococcus, measles, mumps, rubella, varicella, yellow fever, Respiratory syncytial virus, tick borne Japanese encephalitis, pneumococcus, streptococcus, typhoid, influenza, hepatitis, including hepatitis A, B, C and E, otitis media, rabies, polio, HIV, parainfluenza, rotavirus, Epstein Barr Virus, CMV, chlamydia, non-typeable haemophilus, *Moraxella catarrhalis*, human papilloma virus, tuberculosis including BCG, gonorrhea, asthma, atherosclerosis, malaria, *E-coli*, Alzheimer's Disease, *H. Pylori, salmonella*, diabetes, cancer, herpes simplex, human papilloma and like other substances include all of the major therapeutics such as agents for the common cold, Anti-addiction, anti-allergy, anti-emetics, anti-obesity, antiosteoporeteic, anti-infectives, analgesics, anesthetics, anorexics, antiarthritics, antiasthmatic agents, anticonvulsants, anti-depressants, antidiabetic agents, antihistamines, anti-inflammatory agents, antimigraine preparations, antimotion sickness preparations, antinauseants, antineoplastics, antiparkinsonism drugs, antipruritics, antipsychotics, antipyretics, anticholinergics, benzodiazepine antagonists, vasodilators, including general, coronary, peripheral and cerebral, bone stimulating agents, central nervous system stimulants, hormones, hypnotics, immunosuppressives, muscle relaxants, parasympatholytics, parasympathomimetrics, prostaglandins, proteins, peptides, polypeptides and other macromolecules, psychostimulants, sedatives, sexual hypofunction and tranquilizers In an embodiment, the material in the pocket is configured to allow a skin-substance to emerge from the skin surface into the patch.

In an embodiment, the skin substance may react with a component of the material.

Imaging refers to the process of making a visual representation of something by scanning it with a detector or electromagnetic beam or by radiographic techniques.

In an embodiment, the imaging technique is either diagnostic or non-diagnostic or Radiography or Magnetic resonance imaging, Nuclear medicine, Ultrasound, Elastography, Photoacoustic imaging, Tomography, Echocardiography, Functional near-infrared spectroscopy, Magnetic Particle Imaging, Electroencephalography (EEG), Magnetoencephalography (MEG), functional Magnetic Resonance Imaging (fMRI), Positron Emission Tomography (PET) or Optical Imaging.

In an embodiment, the molecular tag may be used for imaging.

In an embodiment in the present invention, the patch is configured to perform imaging analysis of the skin layer at which is the patch is applied. In another embodiment, the imaging is performed of the area where the patch was applied, but after removal of the patch from said area.

In an embodiment, imaging is the technique to take the images after applying or injecting imaging agent on or in the skin.

In an embodiment, the device is configured for an imaging purpose or a localized drug usage or a combination thereof.

The term activation means to start it off, to trigger or to set in motion. By chemical means "activation" refers to the reversible transition of a molecule into a nearly identical chemical or physical state, with the defining characteristic being that this resultant state exhibits an increased propensity to undergo a specified chemical reaction.

In an embodiment, materials are activated for imaging purpose.

In an embodiment, the material in the pocket is configured to be activated in a condition and to react with the skin.

In an embodiment, the material is activated in a condition, comprising a radiation, a heat, a mixing with a second material and/or a combination thereof.

In an embodiment, the second material is either capable of making homogenous or non-homogenous mixture with the material to be activated. The second material is different than the material present inside the pocket and to be activated. The second material activate the material present in the pocket. For example: the material in the pocket is liquid. The second material is also liquid which is miscible with the material in the pocket and helps to activate it.

The term "peeling" refers to a removable of a film or liner without the film or liner breaking, tearing or tearing is also referred to in the food industry as "peeling". The peelability of the film or liner is determined mainly by the properties of the surface layer of the film which is sealed. The peelability of films can be determined relatively easily in the laboratory using a stress-strain tester (e.g., Zwick).

In an embodiment, peelability of peelable liner could be easy peel, medium peel and with strong, resistant peelability (strong peel). For Easy peelability (easy peel) Peel force in the range of about 1 to 4 N per 15 mm strip width Firm peelability (medium peel) Peel force in the range of about 3 to 8 N per 15 mm strip width Strong, resistant peelability (strong peel) Peel force in the range of more than 5 N per 15 mm strip width In an embodiment, peeling of the patch is done after the application of the material on the skin and before the imaging.

In an embodiment, a peelable liner is used on the patch.

In an embodiment, a peelable liner having a specific resin composition and a laminated structure can achieve both a peeling force and a liner lifting deterrence. Further, a particularly excellent pressure-sensitive adhesive sheet can be obtained when the peeling force of the pressure-sensitive adhesive layer and the peelable liner and the rigidity of the peelable liner have a specific relationship.

The term "sensor" is a device, module, machine, or subsystem whose purpose is to detect events or changes in its environment and send the information to other electronics, frequently a computer processor.

In an embodiment, the sensor may be a biosensor. For example, sensor is integrated in the patch for monitoring a glucose concentration in a host and for delivering insulin to a host is provided, the system comprising a continuous glucose sensor, wherein the continuous glucose sensor is configured to substantially continuously measure a glucose concentration in a host, and to provide sensor data associated with the glucose concentration in the host; an electronics module comprising an on/off controller module configured to iteratively determine an insulin therapy instruction in response to an evaluation of a relationship of internally derived data and a glucose boundary, wherein the insulin therapy instruction comprises an instruction selected from the group consisting of on and off; and an insulin delivery device configured to deliver insulin to the host, wherein the insulin delivery device is at least one of physically connected to a receiver and operably connected to a receiver, wherein the insulin delivery device is configured to receive the insulin therapy instruction from the controller.

The term "biosensor" is an analytical device, used for the detection of a chemical substance, that combines a biological component with a physicochemical detector. The sensitive biological element, e.g., tissue, microorganisms, organelles, cell receptors, enzymes, antibodies, nucleic acids, etc., is a biologically derived material or biomimetic component that interacts with, binds with, or recognizes the analyte under study.

In an embodiment, sensors in the patch are wired or wireless. In some applications, the sensor can be wired to a device that is configured to process and/or display information that the sensor acquires. In another example, wireless sensors that communicate with other devices wirelessly are there. The wireless sensor can include a storage device configured to store data collected by the sensor device.

Additionally, or alternatively, the wireless sensor patch can include a transmitter configured to transmit a radio signal received by the device (eg, using Bluetooth radio technology). In an embodiment, the receiving device may be a mobile phone or other receiving device that can relay information by satellite to other locations for processing. In another example, the wireless sensor patch can include a USB port or other interface that allows for a regular wired connection with the wireless sensor patch. In this way, information can be collected continuously by the device in real time (eg, over a wireless connection) in synchronization with the device. It can be sent periodically to the device when performing other direct connections. Such wired or wireless connections can be utilized to download information from the wireless sensor patch to the device, In another example, information or instructions can be uploaded from the device to the wireless sensor patch via a wired or wireless connection. For example, instructions that change the operating conditions of the patch can be uploaded to provide information displayed by the patch and/or other functions.

The term "physiological parameters" defines a parameter or condition to know physiological condition of a user. Exemplary physiological parameters include, but are not limited to, subject body temperature, subject heart rate, subject heart rate variability, subject blood gas levels, subject metabolic rate, subject respiration rate, subject blood analyte levels, subject blood pressure, subject pulse pressure, etc.

In an embodiment, the invention measures a value of a physiological parameter for a subject at a selected state (e.g., state of peak metabolism, state of lowered metabolism, state of rest, etc.), includes obtaining, via a device attached to the subject, a value of the physiological parameter of the subject at a particular time-of-day, and applying a time-dependent relationship function to the obtained physiological parameter value via at least one processor to determine a value of the physiological parameter at the selected state.

In an embodiment, sensor may include pulse oximeter, heart rate sensor, ECG sensor, skin sensors, temperature sensor, blood pressure sensor, impedance sensor, tactile sensor, blood pressure sensor, heart rate sensor, heart rate sensor etc. According to one embodiment, all types of sensors come under the scope of the present invention.

The invention is explained through below various embodiments.

The present invention relates to a device comprising a patch with substrate and adhesive.

An embodiment of the present invention relates to the patch attached to a skin via an adhesive to form a pocket between the patch and the skin. This allows introduction of a material into the pocket, and to hold the material within the pocket. The holding of the material may vary depending on the characteristic of the material, and the utility and application of the material. For example: The material may be held for about 1 second(s), about 2 s, about 3 s, about 4 s, about 5 s and so on; about 1 minute (min), about 2 min, about 3 min, about 4 min, about 5 min and so on; 1 hour, 2-hour, 3 hour, 4 hour, 5 hour and so on.

In an embodiment, patch can include multiple layers. The multiple layers of the patch can be applied sequentially to the breached or non-breached skin, or they can be adhered either completely or partially to each other with the adhesive prior to application to the skin. Generally, the top layer of the patch may be the same size or larger than the underlying layers. The patch can also be in the form of stickers. Further, each layer of patch in the multiple layers may be made up of same substrate or different substrate.

An embodiment of the present invention relates to the patch attached to a skin conspicuously or inconspicuously. To make the stuck portion hard to be inconspicuous, the patch is preferably caused to closely adhere to the skin along the skin surface having fine irregularities such as skin furrows. If the patch is stuck on the skin without closely adhering to the finely irregular surface in a state as if it would rise above the skin, a difference in appearance between the patch and the skin surface around it is marked, and so the stuck portion is conspicuous. To make the stuck portion hard to be inconspicuous, it is preferable that the patch closely adheres to the skin along the irregular surface with skin furrows or the like of a fine texture structure, and the texture structure appears on a surface (back surface of the base layer) of the patch in a state as if it would be transferred to the surface.

In an embodiment, patch possess stretchability. it is also an important subject not to give a feeling of physical disorder during sticking. If the patch is hard to easily follow the movement of the skin, a feeling of physical disorder attributed to the resistance of the patch is caused. In order not to give the feeling of physical disorder during sticking, the patch is required to have stretchability so as to easily follow the movement of the skin surface having fine irregularities.

In an embodiment, the patch of the present invention has moderate adhesive strength, the patch is excellent in balance between adhesion to the skin surface and releasability after use. If the adhesive strength of the patch is too weak, the patch is simply peeled from the skin surface or cannot closely adhere to the skin along the skin surface having fine irregularities such as skin furrows. If the adhesive strength of the patch is too strong, a rash may be caused, or peeling of the patch after use becomes difficult. When each thickness of the base layer, pressure sensitive adhesive layer and patch is thinned, it is liable to encounter a difficulty in achieving the moderate adhesive strength.

In an embodiment, the patch has sensors for monitoring various physiological parameters.

In an embodiment, sensors can include but not limited to temperature sensors, electrocardiogram (ECG) sensors, electrical skin reaction (GSR) sensors, depending on the sensor application.

In an embodiment, the patch is intended as an adherend include medical patches typified by dressing materials for protecting the skin with a damaged site, operation scar or the like; and household patches such as first-aid adhesive bandages, waterproofing patches and protecting patches for protecting the skin. These household patches are also used in medical scenes because of protecting the skin with a damaged site or a hole pierced by a syringe needle or the like.

In an embodiment, patch can have any shape and size, for example not limited to rectangular, triangular, oval or round or any geometric shapes.

In an embodiment, patch comprises a substrate.

Substrate can be fabricated from a synthetic polymer as well as purified a biological polymers or combination thereof.

Appropriate synthetic polymers include organic as well as inorganic polymers without limitation, polyamides (e.g., nylon, Zytel™, Technyl™, Winmark™, Rilsan™, Rilsamid™ Radipol™ (polyamides); PA 6T, Trogamid™, Amodel™ (polyphthalamides); Kevlar™ Nomex™, Teijinconex™, Twaron™ and Technora™ (aromatic polyamides or aramides)), polyesters (e.g. polyimides, polysulfones, polyetherketones, Polyethylene terephthalat and polybenzimidazoles), polystyrenes (Styrene-butadiene rubber, Acrylonitrile butadiene styrene), polyacrylates (Methacrylates, Methyl acrylate, Ethyl acrylate, 2-Chloroethyl vinyl ether, 2-Ethylhexyl acrylate, Hydroxyethyl methacrylate, Butyl acrylate, Butyl methacrylate), vinyl polymers (e.g., polyethylene, polytetrafluoro-ethylene, polypropylene and polyvinyl chloride), polycarbonates, polyurethanes, poly dimethyl siloxanes, cellulose acetates, polymethyl methacrylates, ethylene vinyl acetates, polysulfones, nitrocelluloses, vulcanized rubber, poly-4-hydroxybutyrate (P4HB), polypropylene fumarate (PPF), polyethylene glycol-dimethacrylate (PEG-DMA), beta-tricalcium phosphate (beta-TCP), nonbiodegradable polytetrafluoroethylene (PTFE), PEG-acrylate (PEG-Ac), PEG-vinylsulfone (PEG-VS), polyethylene terephthalate homopolymer, polyethylene terephthalate copolymer, polybutylene terephthalate, polycyclohexylene cyclohexanedicarboxylate, polycyclohexylene terephthalate, and polytrimethylene terephthalate and similar copolymers, foam backings of urethane, polyurethane or the like can be used. In an embodiment, the susbtrate is silicon.

Biological polymers can be naturally occurring or produced in vitro by fermentation and the like. Purified biological polymers can be appropriately formed into a substrate by techniques such as weaving, knitting, casting, molding, extrusion, cellular alignment and magnetic alignment. Suitable biological polymers include, without limitation, alginate, chitosan, cotton, wool, collagen, elastin, silk, keratin, gelatin, polyamino acids, polysaccharides (e.g., cellulose and starch), proteins, natural rubber, pectin, chitin, polyhydroxyalkanoates and copolymers thereof. Some other examples of polymers are poly(lactic acid) (PLA), Polycaprolactone (PCL), poly lactic-co-glycolic acid (PLGA), PEO, poly(vinyl alcohol) (PVA), and polyurethane (PU). Polyglycolic acid (PGA), polyhydroxyalkanoate, natural rubbers (polymers of isoprene), suberin and lignin (complex polyphenolic polymers), cutin and cutan (complex polymers of long-chain fatty acids), melanin, polyethene. polymers can also be nanopolymers either of synthetic or natural or semisynthetic origin.

The synthetic polymers of the present invention may be derived from a biological resource via an indirect route involving one or more intermediate compounds.

Furthermore, the synthetic polymers can be biodegradable or non-biodegradable. Biodegradability is also affected by the number of synthetic molecules attached to each protein, as large numbers of attached synthetic molecules may reduce biodegradability by masking cleavage sites.

Substrates may also include metals. Noble metals like titanium, stainless steel, gold, silver, cobalt, chromium and their alloys thereof may also be included in the substrates. Substrates may also be tissues. For example: without limitation includes pericardial tissues.

In an embodiment, the substrate comprises a non-permeable material and/or a permeable membrane. In an embodiment, the substrate is gas permeable liquid nonpermeable; gas permeable liquid permeable; gas nonpermeable liquid permeable; gas non-permeable, liquid nonpermeable; or selectively permeable and can be solid permeable or nonpermeable also.

In an embodiment, the substrate can be inorganic, organic, synthetic, semi-synthetic or natural.

The substrate of the patch of the device of the present invention can be pure or amalgamation of different substrates. The choice of different substrates or their amalgamation or different variations in the substrate can vary depending on the skin site for the localized use, position in the body i.e. internal or external, environment conditions, individual requirement.

In an embodiment, the substrate can be amalgamation of inorganic and organic or synthetic and natural.

In an embodiment, the adhesive forms interface layer between skin and substrate of patch In another embodiment, the adhesive forms an interface between the first substrate and second substrate with suitable porosity and hydrophilicity. It can be used to fasten the layers of the substrate together and/or to bind the patch to the skin site.

In particular, the adhesive interface should be sufficiently porous such that the adhesive can incorporate into or with the biocompatible material to achieve mechanical interlocking between the two substrates and the adhesive, wherein two substrates can be skin and substrate or different composition substrate.

To form an adhesive bond between any two substrates, a first substrate associated with the adhesive is generally contacted with a second substrate.

In an embodiment, polyurethane adhesives that incorporate aliphatic polycarbonate polyols derived from the copolymerization of epoxides and carbon dioxide are used.

In an embodiment, pressure-sensitive adhesive, an acrylic pressure-sensitive adhesive or a polyether pressure-sensitive adhesive is used from the viewpoint of transparency, processability and durability.

In an embodiment, the adhesive is an UV-cure adhesive. UV-cure adhesives can be solvent borne or a molten adhesive. The adhesive may bond materials at ambient temperature using photoinitiator chemistries that convert absorbed light energy (typically UV light) to chemical energy in the form of initiating species such as free radicals or cations and thereby initiate a polymerization reaction in a monomer-containing adhesive.

In an embodiment, the adhesives contain acrylates or methacrylates. Examples of acrylates and/or methacrylates useful as components of monomer mixture (i) include methyl acrylate, ethyl acrylate, ethyl methacrylate, methyl methacrylate, n-butyl acrylate, n-butyl methacrylate, n-pentyl acrylate, n-hexyl acrylate, n-heptyl acrylate, and n-octyl acrylate, n-nonyl acrylate, lauryl methacrylate, cyclohexyl acrylate, and branched (meth)acrylic isomers, such as i-butyl acrylate, i-butyl methacrylate, n-butyl methacrylate, 2-ethylhexyl acrylate, stearyl methacrylate, and isooctyl acrylate. The exemplary acrylates and/or methacrylates are monoacrylic monomers, and do not include any di or multi-acrylate monomers.

In an embodiment, the adhesive may also comprise various other additives, such as plasticizers, tackifiers, and fillers, all of which are conventionally used in the preparation of Photo-sensitive adhesives (PSAs). As tackifier or tackifying resins to be added, it is possible to use any known tackifying resins described in the literature. Non-limiting examples include pinene resins, indene resins, and their disproportionated, hydrogenated, polymerized, and esterified derivatives and salts, the aliphatic and aromatic hydrocarbon resins, terpene resins, terpene-phenolic resins, C5 resins, C9 resins, and other hydrocarbon resins. Any desired combinations of these or other resins may be used in order to adjust the properties of the resultant adhesive in accordance with the desired final properties.

The acrylic pressure sensitive additive (PSAs) may further be blended with one or more additives such as aging inhibitors, antioxidants, light stabilizers, compounding agents, and/or accelerators.

The adhesive may further be mixed with one or more fillers. Fillers are compounds part of the adhesives and have as objective to vary or determine the chemical, physical and mechanical properties of the adhesives, after selection of the monomers and polymers, fillers take on an important role in the composition of the adhesives.

In an embodiment, fillers can be fibers, carbon black, zinc oxide, titanium dioxide, solid or hollow glass microbeads, microbeads of other materials, silica, silicates, and chalk. In an embodiment, the adhesive may be double-sided self-adhesive sheet.

The adhesive may be transparent or non-transparent.

In an embodiment, the substrate and the adhesive are compatible with DMSO.

In an embodiment, the substrate and/or the adhesive are compatible with the material present inside pocket of the patch.

In an embodiment, the substrate and/or the adhesive are compatible with penetration enhancers.

In an embodiment, the substrate is flexible. The flexible substrate can be polymeric rubber, paper based like kraft paper, diamond coated kraft paper, cotton rag paper, fish paper, vulcanized fiber, polypropylene, PET, polycarbonate, glass epoxy polyimide, elastomeric materials. nylon, polyamide, nylon 6, polyamide 6, Nylon MXD 6, PVOH, PVC, PVDC, PCTFE, sol-gel material, liquid crystal polymer, PA 6, PGA, PHA, PLA, cellulose esters, TPS, PBS, vacuum metal or metal oxide-coated flexible material (such as Al, SiOx, AlOx), nanoclay coating, paper tinsel and their blend, combination. Examples of polymeric rubber bases include one or more of styrene-isoprene-styrene polymers, styrene-olefin-styrene polymers including styrene-ethylene/propylene-styrene polymers, polyisobutylene, styrene-butadiene-styrene polymers, polyisoprene, polybutadiene, natural rubber, silicone rubber, acrylonitrile rubber, nitrile rubber, polyurethane rubber, polyisobutylene rubber, butyl rubber, halobutyl rubber including bromobutyl rubber, butadiene-acrylonitrile rubber, polychloroprene, and styrene-butadiene rubber.

The particular substrate for association with an adhesive can form the entire device or it can form portions of the device. Similarly, different substrates can be combined to form the patch. The selected approaches for association of the adhesive with the substrate or substrates may influence the type of the patch.

In an embodiment, the substrate and adhesive are biocompatible. Biocompatible substrate and adhesive can be organic as well as inorganic. Organic adhesive can be from natural or non-natural sources, natural sources included vegetable starch (dextrin), natural resins or animals (e.g. the milk protein casein and hide based animal glues). Inorganic adhesives include non-carbon based adhesives such as cement and mortar.

A few examples of biocompatible substrates is Polydimethylsiloxane (PDMS), Polylactic acid, poly-ε-caprolactone (PCL) film, triglycidylamine. Biocompatible adhesive can be made up of epoxyamine.

In an embodiment of the present invention, the device further comprises a peelable liner and/or an opening.

In another embodiment, the peelable liner is below the patch and attached to the patch via the adhesive to form the pocket between the patch and the peelable liner.

In an embodiment, peelable liner is made up of biocompatible material. The peelable liner and adhesive can be on the periphery or the inner side of the substrate or to whole area of the patch. The portion of the substrate attached with the adhesive or peelable liner vary depending on the usage requirements of the patch. The periphery constitutes an external portion of the patch. The external portion of the patch can be inferred as a portion covering an area outside the pocket area of the patch. The inner side of the substrate can be inferred as a portion involved in formation of pocket area of the patch.

In an embodiment, the peelable liner has similar composition of the substrate.

In an embodiment the peelable liner showing excellent peel ability, causing no float of the liner even in case of storage in a curved state and showing excellent recyclability, and providing a pressure-sensitive sheet containing the peelable liner.

In an embodiment, peelability of peelable liner could be easy peel, medium peel and with strong, resistant peelability (strong peel). For Easy peelability (easy peel) Peel force in the range of about 1 to 4 N per 15 mm strip width Firm peelability (medium peel) Peel force in the range of about 3 to 8 N per 15 mm strip width Strong, resistant peelability (strong peel) Peel force in the range of more than 5 N per 15 mm strip width.

In an embodiment, a peelable liner having a specific resin composition and a laminated structure can achieve both a peeling force and a liner lifting deterrence. Further, a particularly excellent pressure-sensitive adhesive sheet can be obtained when the peeling force of the pressure-sensitive adhesive layer and the peelable liner and the rigidity of the peelable liner have a specific relationship.

In an embodiment, the peelable liner having a layer structure of at least three layers, wherein one surface layer is a layer made of high-density polyethylene, and the other surface layer is a layer made of low-density polyethylene, and further substantially low density. A peelable liner having an intermediate layer containing only polyethylene as a resin component is provided.

In an embodiment, the peelable liner, which is typically used in the present invention, a film of polyethylene, polypropylene, ethylene vinyl acetate copolymer, vinyl chloride or the like, a metal film prepared by aluminum vapor deposition or the like may be exemplified, and the liner surface may be subjected to a release treatment such as a silicon treatment or the like may be included. As the peelable liner used in the present invention, for example, those having a linear or curved cut, those in which two or more liners overlap in part, those having a turned edge are employed in view of easy release thereof.

In an embodiment, the present invention provides the pressure-sensitive adhesive sheet, wherein the pressure-sensitive adhesive layer is a pressure-sensitive adhesive layer containing bubbles and/or hollow microspheres. The peelable liner and pressure-sensitive adhesive sheet of the present invention are excellent in releasability and do not cause liner lifting even when stored in a curved state. Moreover, since it is a simple structure which does not contain a polar group etc. and each layer consists of polyethylene, it is excellent also in recyclability. In the present invention, the peelable liner and the pressure-sensitive adhesive sheet may each be in the form of a tape, that is, include a release tape material and a pressure-sensitive adhesive tape.

In an embodiment, the peelable liners can be of any shape. Peelable liners may adhered to substantially the entire interior portion of the patch. The interior portion cover the pocket are within the patch. The peelable liners may also defining multiple perforations that may extend therethrough primarily in the central portion of the interior surface, so that the liquid may free-flow through the perforations.

In an embodiment, the peelable liner, adhesives are heat or pressure resistant. In another embodiment, the peelable liner, adhesive or the substrate can be heat or pressure sensitive.

In an embodiment, the opening is a space or a gap that allows passage or access in the device. It leads to the pocket in the patch. The size of the opening can vary from picometer (µm) to millimeter (mm) to cm.

The size of the opening is about 2 µm, about 5 µm, about 10 µm, about 5 nm, about 10 nm, about 50 nm, about 100 nm, about 150 nm, about 200 nm, about 300 nm, about 500 nm, about 750 nm, about 1 µm, about 2 µm, about 3 µm, about 4 µm, about 5 µm, about 6 µm, about 7 µm, about 8 µm, about 9 µm, about 10 µm, about 15 µm, about 20 µm, about 1 mm, about 2 mm, about 3 mm, about 5 mm and more or within a range in between.

In an embodiment, the opening can be of any shape not limited to oval, round, square, rectangular or of any other shape.

In an embodiment, the opening comprises a protrusion or a tubular structure.

In an embodiment, the said protrusion or said tubular structure comprises a clamp configured to open or close the opening.

In an embodiment, clamp can be roller pinch or slide clamp. An improved injection molded plastic roller pinch clamp for Intravenous (IV) sets includes a housing having side walls, a bottom wall, a top wall, a flow control region, a roller wheel and plastic tubing which is pinched between the roller wheel and the bottom wall.

In an embodiment, the roller clamp infuse the liquid/s at a specific flow rate.

In an embodiment, the specific flow rate can be about 1 ml/min, about 2 ml/min, about 3 ml/min, about 5 ml/min etc.

In an embodiment, the slide clamp is used to completely stop the IV from flowing, without having to adjust the roller clamp.

In an embodiment, the flap may comprise composition same as a substrate of patch.

In an embodiment, the flap may comprise different composition than substrate of patch.

In an embodiment, the substrate disclosed for patch, may be employed to fabricate the flap of the patch.

In an embodiment, flap can be fabricated from a synthetic polymer as well as a biological polymer or combination thereof.

Flap may be of the same material as substrate. The flap may also be the same material as the patch. Flap may also include metals. Noble metals like titanium, stainless steel, gold, silver, cobalt, chromium and their alloys thereof may also be included in the making of flap.

In an embodiment, the flap comprises a non-permeable material and/or a permeable membrane.

In an embodiment, the flap of the patch of the device of the present invention can be pure or amalgamation of different polymers.

In an embodiment, the flap can be amalgamation of inorganic and organic or synthetic and natural. The choice of different polymers or their amalgamation or different variations in the polymers can vary depending on the skin site for the localized use, position in the body i.e. internal or external, environment conditions, individual requirement.

In an embodiment, the flap is same as the substrate of the patch.

In another embodiment, the flap is different than the substrate of the patch.

In an embodiment, the flap comprises a net structure to hold a surface tension of a liquid.

The material held inside the pocket has a surface tension to be able to be held within the pocket.

In an embodiment, the flap can hold a liquid at various temperatures that can induce changes in the surface tension of that liquid.

A liquid is a nearly incompressible fluid that conforms to the shape of its container but retains a (nearly) constant volume independent of pressure. It is the state with a definite volume but no fixed shape.

Cohesive forces between molecules cause the surface of a liquid to contract to the smallest possible surface area. This general effect is called surface tension. Surface tension is the tendency of liquid surfaces to shrink into the minimum surface area possible. There are two primary mechanisms in play in surface tension. One is an inward force on the surface molecules causing the liquid to contract. Second is a tangential force parallel to the surface of the liquid. The net effect is the liquid behaves as if its surface were covered with a stretched elastic membrane.

In an embodiment, in net structure fibers are laid along different directions in one plane and along the thickness direction to form 3D net structures. The fabric consists of one or many parallel yarn layers, each of which can be arranged at a different orientation. In an embodiment the net structure can be an open-meshed fabric twisted, knotted, or woven together at regular intervals. Net structure may be hand-woven, non-woven, machine made, or laser cut.

In various embodiments, net structure can be homogenous material layer. In various embodiments, net structure can be laminate structures, wherein at least two material layers is stacked on top of each other. In various embodiments, net structure can have layers, wherein at least three material layers is stacked on top of each other.

In various embodiments, net structure can have laminate structures, wherein at least four material layers are stacked on top of each other. In various embodiments, a part of net structure can be homogenous material layer and another part of identical net structure can be wherein at least two material layer laminate structures stacked on top of each other. In various embodiments the layer of laminate structures can be bonded to each other at least partly. In various embodiments, the layer of laminate structures cannot be bonded to each other.

In an embodiment, the net structure of flap may comprise composition comprising substrate of the patch.

In an embodiment, the net structure of flap can be made of miscellaneous material, such as synthetic fibers (such as polyester fiber or polypropylene Fiber), natural fiber (such as wood-fiber or cotton fiber), the combination of natural fiber and synthetic fibers, porous foam, web shape steep foam, film, apertured plastic film etc. The example of suitable material include but not limited to artificial silk, timber, cotton, polyester, polypropylene, Polyethylene, nylon or other can thermal fiber, two-component staple fiber, polyolefin, such as, but not limited to polypropylene, the copolymer of alkene, the aliphatic (acid) ester of linear low density polyethylene and polylactic acid, fine-meshed film fiber etc., and combination thereof.

Skin is a multi-laminate tissue and an excellent barrier which has evolved to allow any individual to survive in a dry environment. It is the outermost layer, the stratum corneum (SC) which comprises the major barrier to permeation. This use of penetration enhancers overcomes this hurdle. Skin may refer to outermost barrier layer between external environment and intrinsic environment of body a living organism. In an embodiment, the patch may be employed to any living individual not limited to mammals such as humans.

In an embodiment, a material is held within the pocket.

In an embodiment, the material may comprise a penetration enhancer, a conditioning liquid, a molecular dye, a tag, a nanoparticle, a radionucleotide, a drug, a solvent enhancer, ph regulator and/or a combination thereof.

In an embodiment, the conditioning agent includes for example but not limited is cetearyl alcohol, PEG 40 and its other variations, castor Oil, stearalkonium chloride.

In an embodiment, molecular dye includes for example but not limited to poly propylene, polyurethane, reducing dye, acid dyes, disperse dyes, near infrared-II dye (the dye working from 780 nm to 2500 nm) etc.

In an embodiment, radionucletide includes for example but not limited is radioactive uranium based, radioactive thorium based, radioactive bismuth based, radioactive iodine based, radioactive fluorine and like.

In an embodiment, the penetration enhancer includes for example comprises alcohols which consists of short chain alcohols e.g. Ethanol, Isopropyl alcohol; long chain alcohols e,g, Decanol, Hexanol, Lauryl alcohol, Myristyl alcohol, Octanol, Octyl dodecanol, Oleyl alcohol; Amides which consists of cyclic amides e.g. Azone is an azo derivative of ketone (e.g. laurocapram); Esters-Alkyl esters e.g. Ethyl acetate, Benzoic acid esters e.g. Octyl salicyclate, Padimate O, Fatty acid esters e.g. Ethyl oleate, Glyceryl monoleate, Glyceryl monocaprate, Glyceryl tricaprylate Isopropyl myristate, Isopropyl palmitate, Propylene glycol monolaurate, Propylene glycol monocaprylate; Ether alcohols e.g. Transcutol®; Fatty acids e.g. Lauric acid, Linoleic acid, Linolenic acid, Myristic acid, Oleic acid, Palmitic acid, Stearic acid, Isostearic acid; Glycols e.g. Dipropylene glycol, Propylene glycol (a common excipient in topically applied dosage forms), 1,2-butylene glycol, 1,3-butylene glycol; Pyrrolidones—is an organic compound consisting of a 5-membered lactam, making it the simplest γ-lactam. It is a colorless liquid that is miscible with water and most common organic solvents e.g. N-methyl-2-pyrrolidone, 2-pyrrolidone (2P); Sulphoxides also called sulfoxide, is a class of organic compounds containing sulfur and oxygen and having the general formula (RR') SO, in which R and R' are a grouping of carbon and hydrogen atoms. e.g. Decylmethyl sulphoxide, Dimethyl sulphoxide (DMSO), Surfactants (also common in dosage forms) which consist of Anionic surfactants e.g. Sodium lauryl sulphate, Cationic surfactants e.g. Alkyl dimethylbenzyl ammonium halides, Alkyl trimethyl ammonium halides, Alkyl pyridinium halides; Non-ionic surfactants e.g. Brij 36T, Tween 80; Terpenes e.g. Monoterpenes Eugenol, d-Limonene, Menthol, Menthone Sesquiterpenes Farnesol, Neridol.

In an embodiment, the amount of penetration enhancer is about 1 μl, about 2 μl, about 5 μl, about 10 μl, about 25 μl, about 50 μl, about 75 μl, about 100 μl, about 200 μl, about 1 ml, about 2 ml, about 3 ml, about 5 ml or less and more or an amount that could be held within the pocket according to the size of the pocket.

In an embodiment, the size of the pocket is about 2 μm, about 5 μm, about 10 μm, about 5 nm, about 10 nm, about 50 nm, about 100 nm, about 150 nm, about 200 nm, about 300 nm, about 500 nm, about 750 nm, about 1 μm, about 2 μm, about 3 μm, about 4 μm, about 5 μm, about 6 μm, about 7 μm, about 8 μm, about 9 μm, about 10 μm, about 15 μm, about 20 μm, about 1 mm, about 2 mm, about 3 mm, about 5 mm and more or within a range in between.

In an embodiment, the material in the pocket comprises a powder, an enzyme, a growth factor, antiproliferative/antimitotic drugs, a gel, an ampoule containing a unit dose, a conditioning liquid, a molecular dye, a tag, a nanoparticle, a radionucleotide, a granule, a microorganism and/or a combination thereof.

In an embodiment, the therapeutically effective amount of material is present inside the pocket.

The term "therapeutically effective amount" refers to the amount of an agent that will elicit the biological or medical response of cells, tissue, system, or subject that is being sought by the user, researcher, veterinarian, medical doctor, clinician medical staff or technician. The term "effective amount" includes that amount of a compound that, when administered, is sufficient to elliciate to some extent, one or more binding activities between the compound/material in the liquid and an element in the skin, for example, protein, DNA, RNA, etc. The effective amount will vary depending on the agent and the condition to be analyzed.

In an embodiment, the material in the pocket is solid, semi-solid, quasi-solid or liquid or gas.

In an embodiment, the material is liquid.

In an embodiment, the enzyme can be hydrolases, oxidoreductases, lyases, transferases, ligases, proteases, isomerases and/or combinations thereof. The enzyme can be the natural or genetically engineered. The enzyme can be in active or pro-active form. A pro-active form of enzyme is also called as a proenzyme, is an inactive precursor of an enzyme. A zymogen requires a biochemical change (such as a hydrolysis reaction revealing the active site or changing the configuration to reveal the active site) for it to become an active enzyme. e.g., thrombin, fibrinogen.

In an embodiment, wherein the growth factor includes for example but not limited to Adrenomedullin (AM), Angiopoietin (Ang), Autocrine motility factor, Bone morphogenetic proteins (BMPs), Ciliary neurotrophic factor family, Ciliary neurotrophic factor (CNTF), Leukemia inhibitory factor (LIF), Interleukin-6 (IL-6), Colony-stimulating factors, Macrophage colony-stimulating factor (M-CSF), Granulocyte colony-stimulating factor (G-CSF), Granulocyte macrophage colony-stimulating factor (GM-CSF), Epidermal growth factor (EGF), Ephrins, Erythropoietin (EPO), Fibroblast growth factor (FGF), Foetal Bovine Somatotrophin (FBS), GDNF family of ligands, Glial cell line-derived neurotrophic factor (GDNF), Neurturin, Persephin, Artemin, Growth differentiation factor-9 (GDF9), Hepatocyte growth factor (HGF), Hepatoma-derived growth factor (HDGF), Insulin, Insulin-like growth factors, Interleukins, Keratinocyte growth factor (KGF), Migration-stimulating factor (MSF), Macrophage-stimulating protein (MSP), also known as hepatocyte growth factor-like protein (HGFLP), Myostatin (GDF-8), Neuregulins, Neurotrophins, Brain-derived neurotrophic factor (BDNF), Nerve growth factor (NGF), Neurotrophin-3 (NT-3), Neurotrophin-4 (NT-4), Placental growth factor (PGF), Platelet-derived growth factor (PDGF), Renalase (RNLS)—Anti-apoptotic survival factor, T-cell growth factor (TCGF), Thrombopoietin (TPO), Transforming growth factors, Tumor necrosis factor-alpha (TNF-α), Vascular endothelial growth factor (VEGF), plant growth factors like Indole acetic acid, cytokinin, ethylene, gibberellins, abscisic acid.

In an embodiment, antiproliferative/antimitotic drugs and prodrugs include natural products such as vinca alkaloids (e.g., vinblastine, vincristine, and vinorelbine), paclitaxel, epidipodophyllotoxins (e.g., etoposide, teniposide), antibiotics (e.g., actinomycins, daunorubicin, doxorubicin and idarubicin), anthracyclines, mitoxantrone, bleomycins, plicamycin (mithramycin) and mitomycin, enzymes (e.g., L-asparaginase); antiplatelet prodrugs; antiproliferative/antimitotic alkylating prodrugs such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), triazenes, dacarbazine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine (cladribine); platinum coordination complexes (cisplatin, carboplatin), procarbazine, hydroxyurea, mitotane, aminoglutethimide; hormones (e.g., estrogen, progestin); anticoagulants (e.g., heparin, synthetic heparin salts and other inhibitors of thrombin); fibrinolytic prodrugs such as tissue plasminogen activator, streptokinase and urokinase, aspirin, dipyridamole, ticlopidine, clopidogrel, abciximab; antimigratory; antisecretory (breveldin); anti-inflammatory agents such as corticosteroids (cortisol, cortisone, fludrocortisone, flucinolone, prednisone, prednisolone, methylprednisolone, triamcinolone, betamethasone, and dexamethasone), NSAIDS (salicylic acid and derivatives, aspirin, acetaminophen, indole and indene acetic acids (indomethacin, sulindac and etodalac), heteroaryl acetic acids (tolmetin, diclofenac, and ketorolac), arylpropionic acids (e.g., ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives (e.g., cyclosporine, tacrolimus (FK-506), sirolimus (rapamycin), azathioprine, and mycophenolate mofetil); angiogenic agents such as vascular endothelial growth factor (VEGF), fibroblast growth factor (FGF); angiotensin receptor blocker; nitric oxide donors; anti-sense oligionucleotides and combinations thereof; cell cycle inhibitors, mTOR inhibitors, and growth factor signal transduction kinase inhibitors.

In an embodiment, wherein the powder or enzyme or microorganism or in general, material can be lyophilized or in any other form. In an embodiment, the microorganism can be archaebacteria, bacteria, fungi, protozoa etc.

In an embodiment, conditioning liquid includes for example but not limited to Isopropyl Myristate (IPM); Sodium Lauryl Sulphate (SLS); Triethanolamine (TEA); Linoleic Acid (LA); Sodium Cocoyl Isethionate (SCI); Sodium Dodecyl Sulphate (SDS); Polyethylene Glycols (PEGs); Sorbitan Sesquioleate (SSO); Glycolic Acid (GA); Retinaldehyde (RAL); Alpha-Hydroxy Acids (AHA); Beta Hydroxy Acid (BHA); Hydrophobically Modified Polymers (HMPs); Natural Moisturizing Factors (NMF) and more.

In an embodiment, the molecular dyes includes for example but not limited to FITC (fluorescein) dyes, PE (R-phycoerythrin), dyes NIR-I (Near Infra-red-I) dyes, NIRII dyes, Polymethine dyes, Cyanine Dyes, hydrophilic dyes, hydrophobic dyes, DNA, RNA or protein dyes, inorganic or organic dyes, natural or synthetic dyes.

In an embodiment, the tag used includes any well-known molecular tag used for imaging.

In an embodiment, the material in the pocket such as liquid is configured to be activated in a condition and to react with the skin.

In an embodiment, the condition for activation of the material includes for example but not limited to comprises a chemical, a radiation-electromagnetic, ionizing, non-ionizing, a heat, a mixing with a second material and/or a combination thereof.

In an embodiment, radiation can be any electromagnetic, acoustic, particle and gravitational radiation. Heat sources can be the use of radiation or the heat pouches in the patch. Heat sources are used to bring the temperature of the patch to about 20° C., about 25° C., about 30° C., about 35° C., about 37° C., about 40° C., about 45° C., about 50° C. and so on and a range in between.

In an embodiment, the second material is either capable of making homogenous or non-homogenous mixture with the material to be activated. The second material is different than the material present inside the pocket and to be activated. The second material activate the material present in the pocket. For example: the material in the pocket is liquid. The second material is also liquid which is miscible with the material in the pocket and helps to activate it.

In an embodiment, the patch is placed on a non-breached skin surface and/or a breached skin surface. The breached skin is a broken, ruptured, wounded or torn conditioned skin In an embodiment, the non-breached skin is intact skin while the breached skin is a broken, ruptured, wounded or torn conditioned skin or a skin having sutures.

In an embodiment, the device is configured for an imaging purpose or a localized drug usage or a combination thereof.

In an embodiment, the imaging technique is either diagnostic or non-diagnostic or Radiography or Magnetic resonance imaging, Nuclear medicine, Ultrasound, Elastography, Photoacoustic imaging, Tomography, Echocardiography, Functional near-infrared spectroscopy, Magnetic Particle Imaging, Electroencephalography (EEG), Magnetoencephalography (MEG), functional Magnetic Resonance Imaging (fMRI), Positron Emission Tomography (PET) or Optical Imaging.

In an embodiment, the present invention relates to a method comprising:
 a. fixing a patch of a device to a skin forming a pocket between the skin and the patch;
 b. introducing a material into the pocket; and
 c. allowing the material to react with the skin,
 wherein the patch comprising a substrate, an adhesive and an opening in the substrate.

In an embodiment, the material in the pocket is configured to be activated.

In an embodiment, the material is activated in a condition comprising a radiation, a heat, a chemical reaction, a mixing with a second material and/or a combination thereof.

In an embodiment, time of application of device is 10 s, 20 s, 30 s, 40 s. 50 s and so on; 1 min 2 min, 3 min, 4 min, 5 min, 10 min and soon; 1 hr, 2 hr, 3 hr, 4 hr, 5 hr and soon.

In an embodiment, a material is applied on skin and then wiped off. The composition of material may be same as composition of material in pocket of patch or different than composition of material present in the pocket.

In an embodiment, time of application of the material is 10 s, 20 s, 30 s, 40 s. 50 s and so on; 1 min 2 min, 3 min, 4 min, 5 min, 10 min and so on; 1 hr, 2 hr, 3 hr, 4 hr, 5 hr and so on.

In an embodiment, Incubation period is defined as the time between application of patch and penetration or absorption of material inside skin. Such time may vary from 10 s, 20 s, 30 s, 40 s. 50 s and so on; 1 min 2 min, 3 min, 4 min, 5 min, 10 min and so on; 1 hr, 2 hr, 3 hr, 4 hr, 5 hr and so on. The incubation period may be symptoms of penetration of the material inside skin and its reaction with the biological moieties present inside body of a patient.

In an embodiment, time of imaging after wiping the material is 10 s, 20 s, 30 s, 40 s. 50 s and so on; 1 min 2 min, 3 min, 4 min, 5 min, 10 min and so on; 1 hr, 2 hr, 3 hr, 4 hr, 5 hr and so on.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability.

The present disclosure is further described by reference to the following exemplary embodiments and examples. These exemplary embodiments and examples are provided for purposes of illustration only and are not intended to be limiting unless otherwise specified. Thus, the present disclosure should in no way be construed as being limited to the following exemplary embodiments and examples, but rather, should be construed to encompass any and all variations which become evident as a result of the teaching provided herein.

Example 1

A silicon patch is placed on the skin above the area to undergo evaluation. A skin conditioning liquid is applied for 1 minute through the opening. Next the fluorescent dye is added to the opening and allowed to incubate for an additional 4 minutes.

After the incubation period, the patch and the liquids are removed and wiped off.

Figure 5:
FIG. 5 shows an embodiment of the skin after applying and removing the patch.

A fiducial is placed adjacent to the area where the patch was placed as shown in FIG. 5. A fiducial marker or fiducial is an object placed in the field of view of an imaging system which appears in the image produced, for use as a point of reference or a measure. It may be either something placed into or on the imaging subject, or a mark or set of marks in the reticle of an optical instrument.

Figure 6:
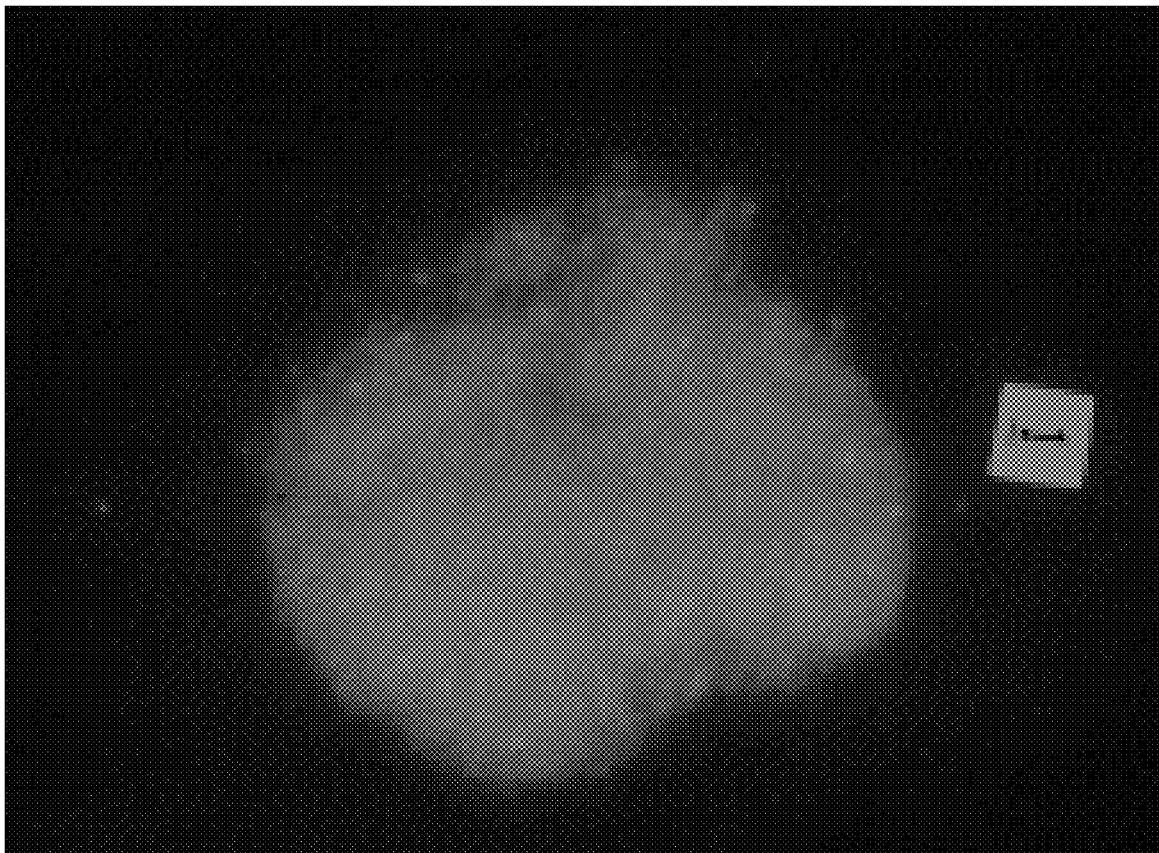
FIG. 6 shows an embodiment of the fluorescent image of the skin.

Photographic and fluorescent images of the skin are captured as shown in FIG. 6 and used for analysis.

All publications, patents and patent applications cited in this specification are incorporated herein by reference in their entireties as if each individual publication, patent or patent application were specifically and individually indicated to be incorporated by reference. While the foregoing has been described in terms of various embodiments, the skilled artisan will appreciate that various modifications, substitutions, omissions, and changes may be made without departing from the spirit thereof.

REFERENCES

1. U.S. Ser. No. 00/510,9874A
2. U.S. Pat. No. 10,245,272 B2
3. US 2009/0043236 A1
4. U.S. Pat. No. 10,245,272 B2
5. US20200405331A1
6. US20030124293A1
7. US20180161252A1

8. U.S. Ser. No. 10/739,908B2
9. U.S. Ser. No. 10/835,672B2
10. U.S. Pat. No. 7,395,111B2
11. U.S. Pat. No. 7,582,069B2

What is claimed is:

1. A device comprising a patch comprising:
   (i) a substrate, wherein the substrate is selected from the group consisting of ethane-acetic acid ethenyl ester, polyvinyl alcohol, ethyl cellulose, Polylactic acid, poly-ε-caprolactone (PCL) film and triglycidylamine;
   (ii) an adhesive on the substrate, wherein the adhesive is selected from the group consisting of an epoxyamine, methyl acrylate, ethyl acrylate, ethyl methacrylate, methyl methacrylate, n-butyl acrylate, n-butyl methacrylate, n-pentyl acrylate, n-hexyl acrylate, n-heptyl acrylate, and n-octyl acrylate, and a branched (meth) acrylic isomer selected from i-butyl acrylate, i-butyl methacrylate, n-butyl methacrylate, 2-ethylhexyl acrylate, stearyl methacrylate or isooctyl acrylate;
   (iii) a pocket under the substrate prefilled with a first material and a second material, wherein the first material is a combination of penetration enhancer and dye; wherein the penetration enhancer is selected from the group consisting of ethanol, isopropyl alcohol, decanol, hexanol, lauryl alcohol, myristyl alcohol, octanol, octyl dodecanol, oleyl alcohol;
   (iv) an opening in the substrate, and
   (v) a flap, wherein the flap covers the opening and is different than the substrate, and is configured for the introduction of materials in the patch; and
   wherein the patch is configured to:
   (a) attach to a skin via the adhesive to form the pocket between the patch and a skin, wherein the adhesive circumscribes the pocket,
   (b) allow introduction of a second material into the pocket through the opening, and
   (c) hold the first material and the second material within the pocket;
   wherein the first material is configured to activate under a specific condition by reacting the first material with the second material; wherein the device is configured to image a portion of the skin on which the patch is placed.

2. The device of claim 1, wherein the device further comprises a peelable liner.

3. The device of claim 2, wherein the peelable liner is below the patch and attached to the patch via the adhesive to form the pocket between the patch and the peelable liner.

4. The device of claim 1, wherein the flap comprises a net structure to hold a surface tension of a liquid.

5. The device of claim 1, wherein the substrate and the adhesive are compatible with the first material and the second material.

6. The device of claim 1, wherein the substrate and the adhesive are compatible with DMSO.

7. The device of claim 1, wherein the substrate is flexible.

8. The device of claim 1, wherein the dye comprises a molecular dye, a tag, a nanoparticle, a radionucleotide, or a combination thereof.

9. The device of claim 1, wherein the pocket comprises a space or a pattern.

10. The device of claim 1, wherein the opening comprises a protrusion or a tubular structure.

11. The device of claim 10, wherein said protrusion or said tubular structure comprises a clamp configured to open or close the opening.

12. The device of claim 1, wherein the patch is configured to allow a skin-substance to emerge from the skin into the patch.

13. The device of claim 1, wherein the specific condition comprises an ionizing radiation.

14. The device of claim 1, wherein the activation of the first material allows the first material to react with the skin for imaging of the skin.

15. The device of claim 1, further comprising a heat pouch within the patch configured to heat the patch.

16. The device of claim 1, wherein the patch is configured to hold a material inside the pocket by a surface tension.

* * * * *